United States Patent
Chang et al.

(10) Patent No.: US 10,416,153 B2
(45) Date of Patent: Sep. 17, 2019

(54) CHEMICAL FLUORESCENT PROBES FOR DETECTING BIOFILMS

(71) Applicants: Nanyang Technological University, Singapore (SG); Agency for Science, Technology and Research, Singapore (SG); National University of Singapore, Singapore (SG)

(72) Inventors: Young-Tae Chang, Singapore (SG); Jun-Young Kim, Singapore (SG); Sahu Srikanta, Singapore (SG); Michael Christian Givskov, Singapore (SG); Liang Yang, Singapore (SG)

(73) Assignees: NANYANG TECHNOLOGICAL UNIVERSITY, Singapore (SG); AGENCY FOR SCIENCE, TECHNOLOGY AND RESEARCH, Singapore (SG); NATIONAL UNIVERSITY OF SINGAPORE, Singapore (SG)

( * ) Notice: Subject to any disclaimer, the term of this patent is extended or adjusted under 35 U.S.C. 154(b) by 0 days.

(21) Appl. No.: 15/568,727

(22) PCT Filed: Apr. 20, 2016

(86) PCT No.: PCT/SG2016/050182
§ 371 (c)(1),
(2) Date: Oct. 23, 2017

(87) PCT Pub. No.: WO2016/171619
PCT Pub. Date: Oct. 27, 2016

(65) Prior Publication Data
US 2018/0143185 A1 May 24, 2018

(30) Foreign Application Priority Data
Apr. 24, 2015 (SG) .......................... 10201503224Q

(51) Int. Cl.
*G01N 33/533* (2006.01)
*C07F 5/02* (2006.01)
*A61K 49/00* (2006.01)
*G01N 33/569* (2006.01)

(52) U.S. Cl.
CPC ....... *G01N 33/533* (2013.01); *A61K 49/0021* (2013.01); *C07F 5/02* (2013.01); *G01N 33/56911* (2013.01); *G01N 2333/21* (2013.01)

(58) Field of Classification Search
CPC ................................. G01N 33/533; C07F 5/02
See application file for complete search history.

(56) References Cited

FOREIGN PATENT DOCUMENTS

| WO | 2012/071012 A2 | 5/2012 |
| WO | 2012/072980 A1 | 6/2012 |
| WO | 2013/095205 A1 | 6/2013 |

OTHER PUBLICATIONS

Roberta J. Worthington et al., Small molecule control of bacterial biofilms, Organic & Biomolecular Chemsitry, 10, 7457-7474. (Year: 2012).*
Anastasiadis et al., "Detection and quantification of bacterial biofilms combining high-frequency acoustic microscopy and targeted lipid microparticles," *Journal of Nanobiotechnology* 12(24): 2014, 11 page.
Caruso et al., "Synthesis and antibacterial activity of novel cationic BODIPY photosensitizers," *Journal of Photochemistry and Photobiology B: Biology* 114:44-51, 2012.
Department of Health and Human Services, "Immunology of Biofilms (R01)," downloaded from https://grants.nih.gov/grants/guide/pafiles/PA-07-288.html on Jan. 18, 2018, 22 pages.
Kang et al., "Visualization and Isolation of Langerhans Islets by a Fluorescent Probe PiY," *Angewandte Chimie International Edition* 52:8557-8560, 2003.
Kim et al., "Detection of Pathogenic Biofilms with Bacterial Amyloid Targeting Fluorescent Probe, CDy11," *Journal of the American Chemical Society* 138:402-407, 2016.
Li et al., "The importance of the viable but non-culturable state in human bacterial pathogens," *Frontiers in Microbiology* 5: 2014, 20 pages.
Ma et al., "*Pseudomonas aeruginosa* Psl Is a Galactose- and Mannose-Rich Exopolysaccharide,"*Journal of Bacteriology* 189(22):8353-8356, 2007.
National Institute of Health, "NIH Guide: Research on Microbial Biofilms," downloaded from https://grants.nih.gov/grants/guide/pafiles/PA-03-047.html on Jan. 18, 2018, 12 pages.
Orlandi et al., "Antimicrobial and anti-biofilm effect of a novel BODIPY photosensitizer against Pseudomonas aeruginosa PAO1,"*Biofouling* 30(8):883-891, 2014.

(Continued)

*Primary Examiner* — Michael G. Hartley
*Assistant Examiner* — Jagadishwar R Samala
(74) *Attorney, Agent, or Firm* — Seed IP Law Group LLP

(57) ABSTRACT

The present invention relates to a family of fluorescent compounds based on the BODIPY scaffold, and methods for the preparation of said compounds. The present invention further relates to the use of said compounds for the detection of bacterial biofilms, wherein the bacterial biofilm comprises *Pseudomonas aeruginosa* and the compound specifically binds to a Fap protein of *Pseudomonas aeruginosa*, or wherein the compound specifically binds to bacterial cells that contain high levels of cyclic-di-guanosine-monophosphate (c-di-GMP).

9 Claims, 12 Drawing Sheets

(56) References Cited

OTHER PUBLICATIONS

Trachoo, "Biofilms and the food industry," *Songklanakarin J. Sci. Technol.* 25:807-815, 2003.
Zhai et al., "Synthesis of a Novel BODIPY Library and Its Application in the Discovery of a Fructose Sensor," *ACS Combinatorial Science* 14:81-84, 2012.
Extended European Search Report, dated Nov. 10, 2018, for European Patent Application 16783506.5, 8 pages.

* cited by examiner (A)

(B)

Figure 2 (B) (continued)
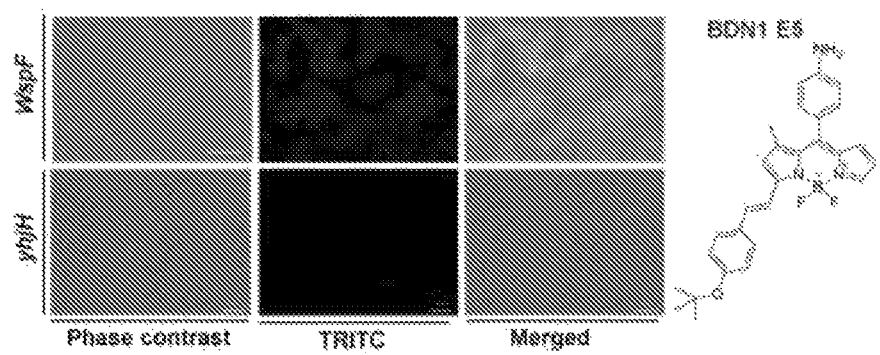
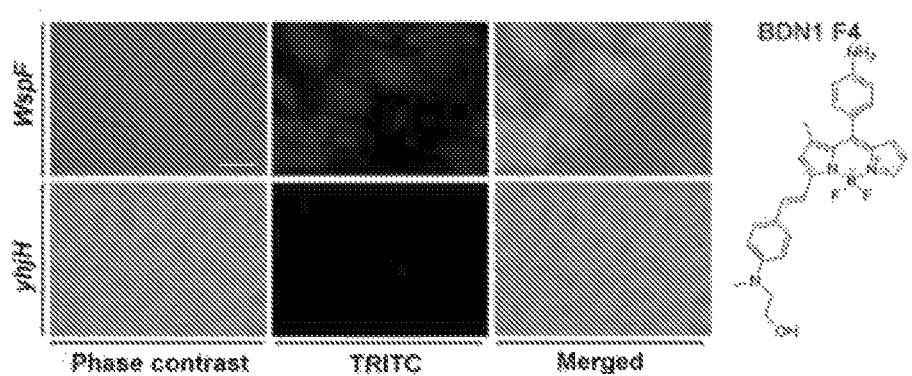
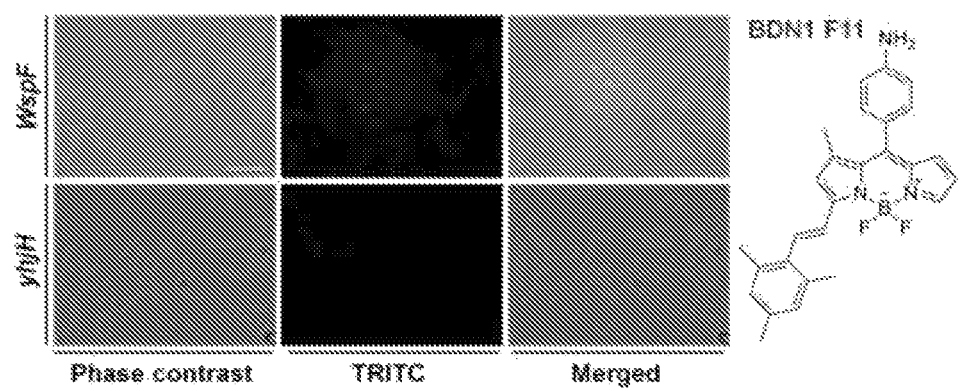

(B)

Figure 4 (B) (continued)
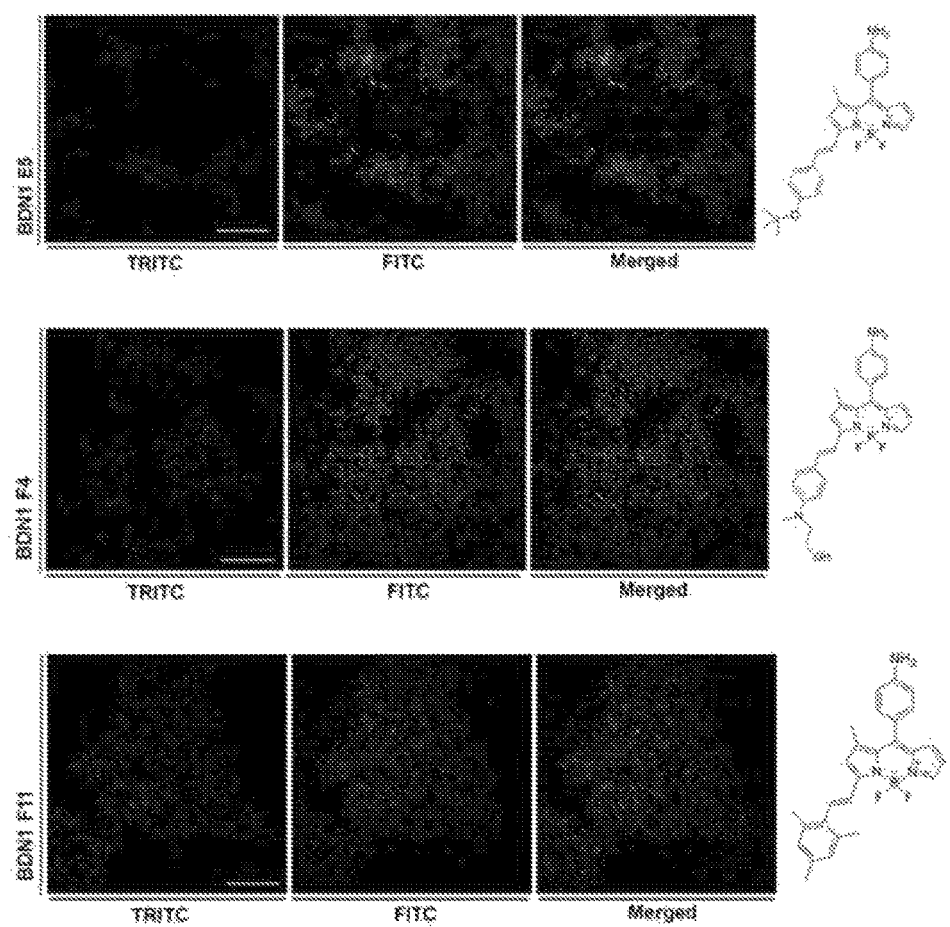

CHEMICAL FLUORESCENT PROBES FOR DETECTING BIOFILMS

FIELD OF THE INVENTION

The present invention lies in the field of biochemistry and relates to compounds that are capable of detecting biofilms and having a structure as described herein. Further, the present invention relates to methods for the preparation of the compounds of the present invention and the use of said compounds for the detection of bacterial biofilms.

BACKGROUND OF THE INVENTION

Biofilms are surface-attached microbial communities which are usually formed by microorganisms when they are exposed to unfavorable conditions for survival. Biofilm formation mechanisms are the subject of current investigations, however, yet biofilm formation and composition are not fully understood due to its quite complicated formation dynamics and highly heterogeneous composition including extracellular DNA, proteins and carbohydrates present in the biofilm matrix. As a densely populated community, bacteria are protected from unfavorable conditions within the complex structure of a biofilm. Because of the protective role of the biofilm matrix and bacterial heterogeneity in particular with respect to physiological adaptations, it is impossible to completely eradicate biofilms even after exposure to the highest deliverable doses of antibiotics.

Also, there is no convenient diagnostic tools to identify the presence of biofilms in a host organism. One available technique is to use fluorescence in situ hybridization techniques but, this can only be done by means of biopsies from tissue that are suspected to contain bacterial biofilms. Molecular tools that enables elucidation biofilm formation mechanisms and the identification—visualization of already formed biofilms are very important for academic purposes and clinical applications.

According to the National Institute of Health, more than 80% of all infections are associated with biofilms [Immunology of Biofilms (PA-07-288); NIH, Department of Health and Human Services, 2007-01-09]. Furthermore, biofilm bacteria are able to disperse and spread to new areas [Research on Microbial Biofilms (PA-03-047); NIH, National Heart, Lung, and Blood Institute, 2002-12-20]. Bacteria in biofilm-associated infections often appear non-cultureable [Li, L.; Mendis, N.; Trigui, H.; Oliver, J. D.; Faucher, S. P. Front. Microbiol. 2014, 5, 258]. Therefore, rapid and reliable identification of biofilm-associated infections are important for choosing the proper treatment strategy in the clinics, such as antimicrobial administration or surgical removal of the infected tissue.

The biofilm matrix (in which the bacteria are embedded) consists of extracellular polymeric substances (EPS) including DNA, proteins and polysaccharides. Several compounds have been reported to specifically label EPS components. For example, DNA staining dyes such as ethidium bromide, Syto9 or DAPI are frequently used to localize extracellular DNA in biofilms [Trachoo, N. Songklanakarin J. Sci. Technol. 2003, 25, 807]. Hippeastrum Hybrid (Amaryllis) Lectin, HHA, that specifically binds to either 1,3- or 1,6-linked mannosyl units in polysaccharides is used for biofilm detection after conjugating with a fluorophore due to its binding specificity with the Psl polysaccharide, a key components of P. aeruginosa biofilms [Ma, L.; Lu, H.; Sprinkle, A.; Parsek, M. R.; Wozniak, D. J. J. Bacteriol. 2007, 189, 8353].

Recently, ligand targeted ultrasound contrast agents (UCAs) were reported to detect biofilm in vitro under high-frequency scanning acoustic miscroscopy [Anastasiadis, P.; Mojica, K. D.; Allen, J. S.; Matter, M. L. J. Nanobiotechnol. 2014, 12, 24]. Even though it showed the possibility as a biofilm detecting tool of application, there is no established method for non-destructive in vivo biofilm detection by imaging so far.

SUMMARY OF THE INVENTION

It is an object of the present invention to meet the above need by providing the compounds of the present invention, which allow for the non-destructive detection of bacterial biofilms. Surprisingly, the present inventors have found that these fluorescent compounds allow the detection of bacterial biofilms in vivo. The sensors are based on a boron-dipyrromethene (BODIPY) scaffold. As these compounds represent a completely new chemical class of biofilm detection compounds, they provide a promising basis for the development of biofilm diagnostic tools.

In a first aspect, the present invention is thus directed to a compound having the structure of formula (I)

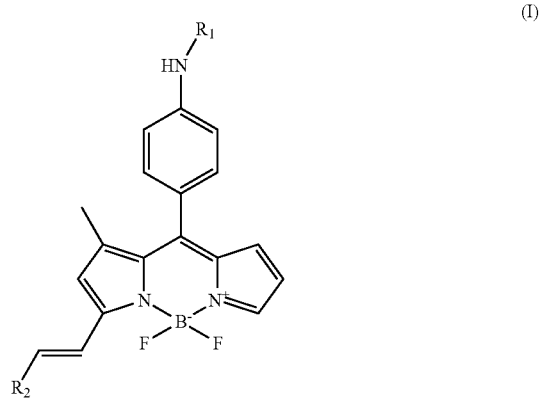

wherein $R_1$ is H or C(O)—$R_3$, $R_3$ is $C_{1-10}$ alkyl, and $R_2$ is substituted or unsubstituted $C_{6-14}$ aryl or a 5-8 membered heteroaryl group comprising 1-4 heteroatoms selected from the group consisting of N, O and S.

In various embodiments of the invention, $R_2$ is

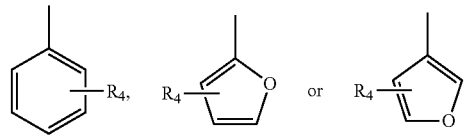

and $R_4$ is selected from the group consisting of H, halogen, alkoxy, hydroxy, nitrobenzene, benzene and tertiary amine.

In further various embodiments of the invention, the compound of the invention is selected from the group consisting of (1)
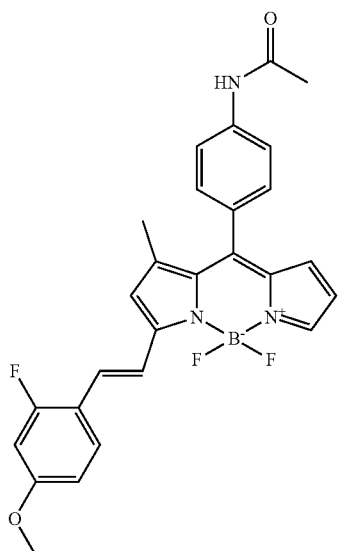
(2)
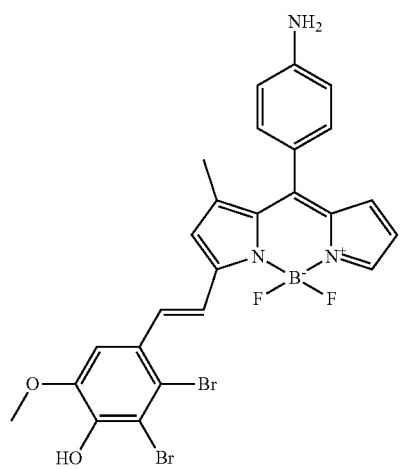
(3)
(4)
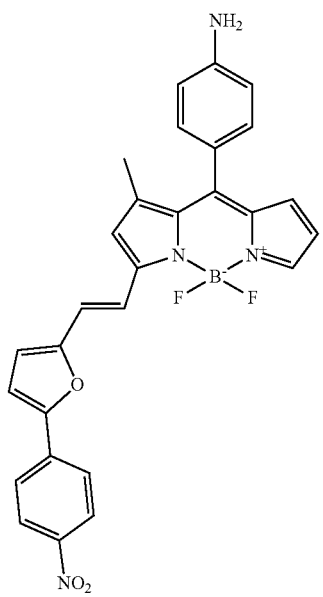
(5)
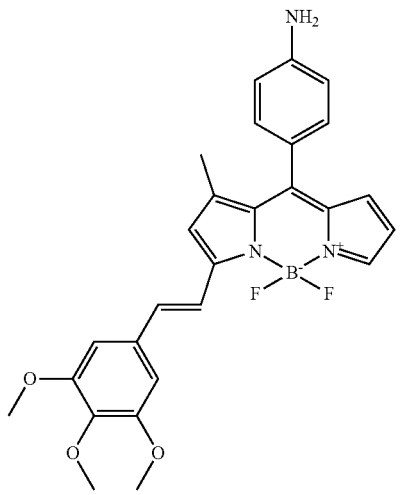
(6)
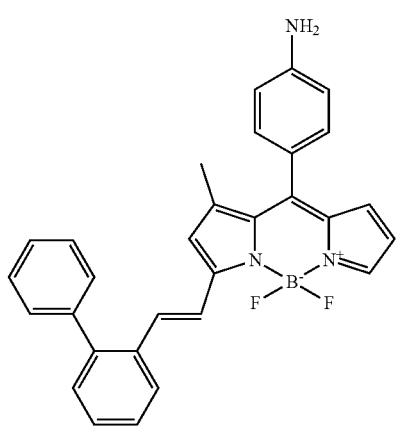

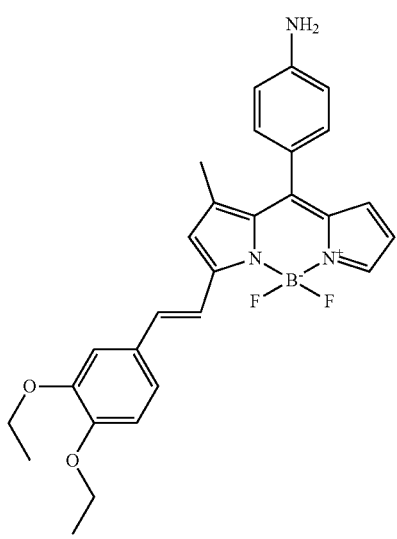 (7)
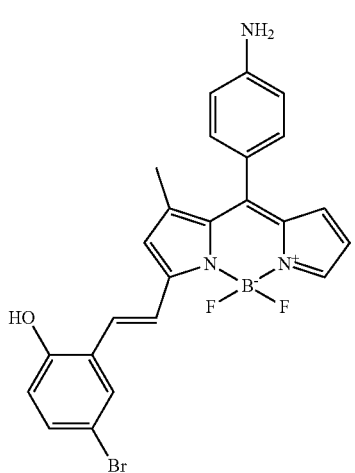 (8)
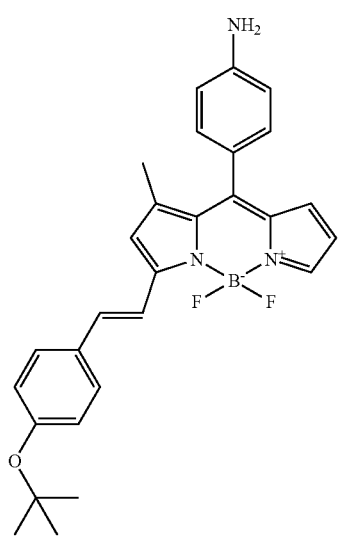 (9)
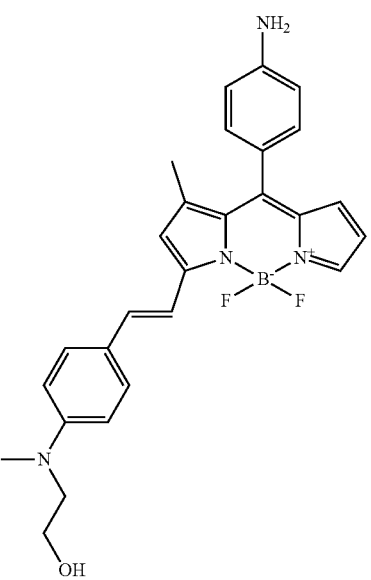 (10)
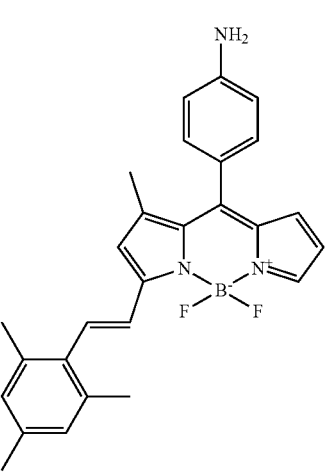 (11)
In a second aspect of the invention, the invention relates to a method for the preparation of a compound of the present invention, comprising:
a) reacting the compound of formula (II) with the compound of formula (III) to form the compound of formula (IV)
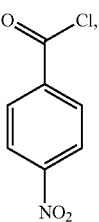 (II)
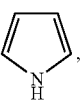 (III)

-continued

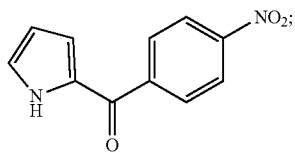
(IV)

b) reducing the compound of formula (IV) to form the compound of formula (V)

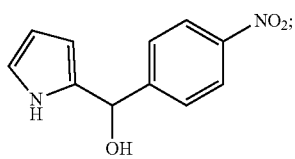
(V)

c) reacting the compound of formula (V) with the compound of formula (VI) to form the compound of formula (VII)

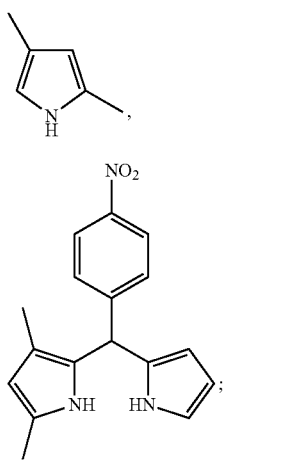
(VI)

(VII)

d) reacting the compound of formula (VII) with boron trifluoride diethyl etherate to form the compound of formula (VIII)

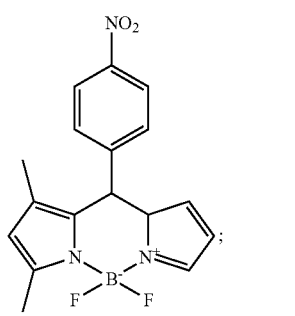
(VIII)

e) reacting the compound of formula (VIII) with $NH_2NH_2$ to form the compound of formula (IX)

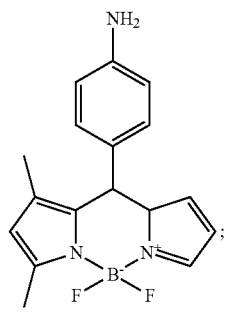
(IX)

f) reacting the compound of formula (IX) with $R_2$—CHO to form the compound of formula (X)

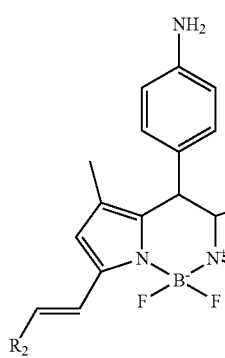
(X)

g) and optionally reacting the compound of formula (X) with $HCO_2R_3$ to form the compound of formula (XI)

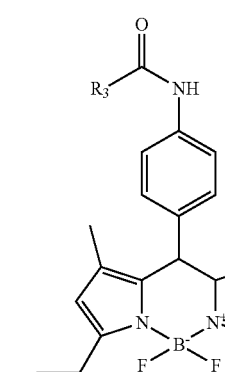
(XI)

wherein
$R_2$ is substituted or unsubstituted $C_{6-14}$ aryl or a 5-8 membered heteroaryl group comprising 1-4 heteroatoms selected from the group consisting of N, O and S; and
$R_3$ is $C_{1-10}$ alkyl.

In various embodiments of the preparation method of the invention, step (a) is carried out at 25 to 78° C. for 2 to 5 h; step (b) is carried out at 0 to 25° C. for 15 to 60 minutes; step (c) is carried out for 2 to 6 h; step (d) comprises a first reaction reacting the compound of formula (VII), toluene, dichloromethane for 20 to 60 minutes and a second reaction reacting the product of the first reaction with 2,3-dichloro-5,6-dicyano-1,4-benzoquinone and triethanolamine at 20 to 25° C. for 6 to 10 h; step (e) is carried out at 80 to 100° C. for 3 to 5 h; step (f) is carried out at 80 to 90° C.; and/or step (g) is carried out at 20 to 25° C. for 2 to 4 h.

In a third aspect, the present invention relates to the use of a compound of the present invention for the detection of bacterial biofilms.

In various embodiments of the invention, the bacterial biofilm comprises Pseudomonas aeruginosa.

In further various embodiments of the invention, an outer cellular amyloid protein structure is detected or, alternatively, the compound specifically binds to bacterial cells that contain high levels of cyclic-di-guanosine-monophosphate (GMP). In various embodiments, the bacterial film is detected in an eye sample or a lung sample.

In still further various embodiments, the detection limit is $8 \times 10^8$ CFU/ml. In various embodiments of the invention, the compound specifically binds to a Fap protein of Pseudomonas aeruginosa.

In various embodiments, the biofilm is detected on a silicon surface and/or the biofilm is detected on the surface of a contact lens, catheter or implant device.

In various embodiments of the invention, the bacteria of the biofilm are detected in vivo.

BRIEF DESCRIPTION OF THE DRAWINGS

The invention will be better understood with reference to the detailed description when considered in conjunction with the non-limiting examples and the accompanying drawings.

FIG. 1 (B) shows a synthetic scheme for high level of cyclic-di-GMP targeting biofilm sensors.

DETAILED DESCRIPTION OF THE INVENTION

Figure 1:
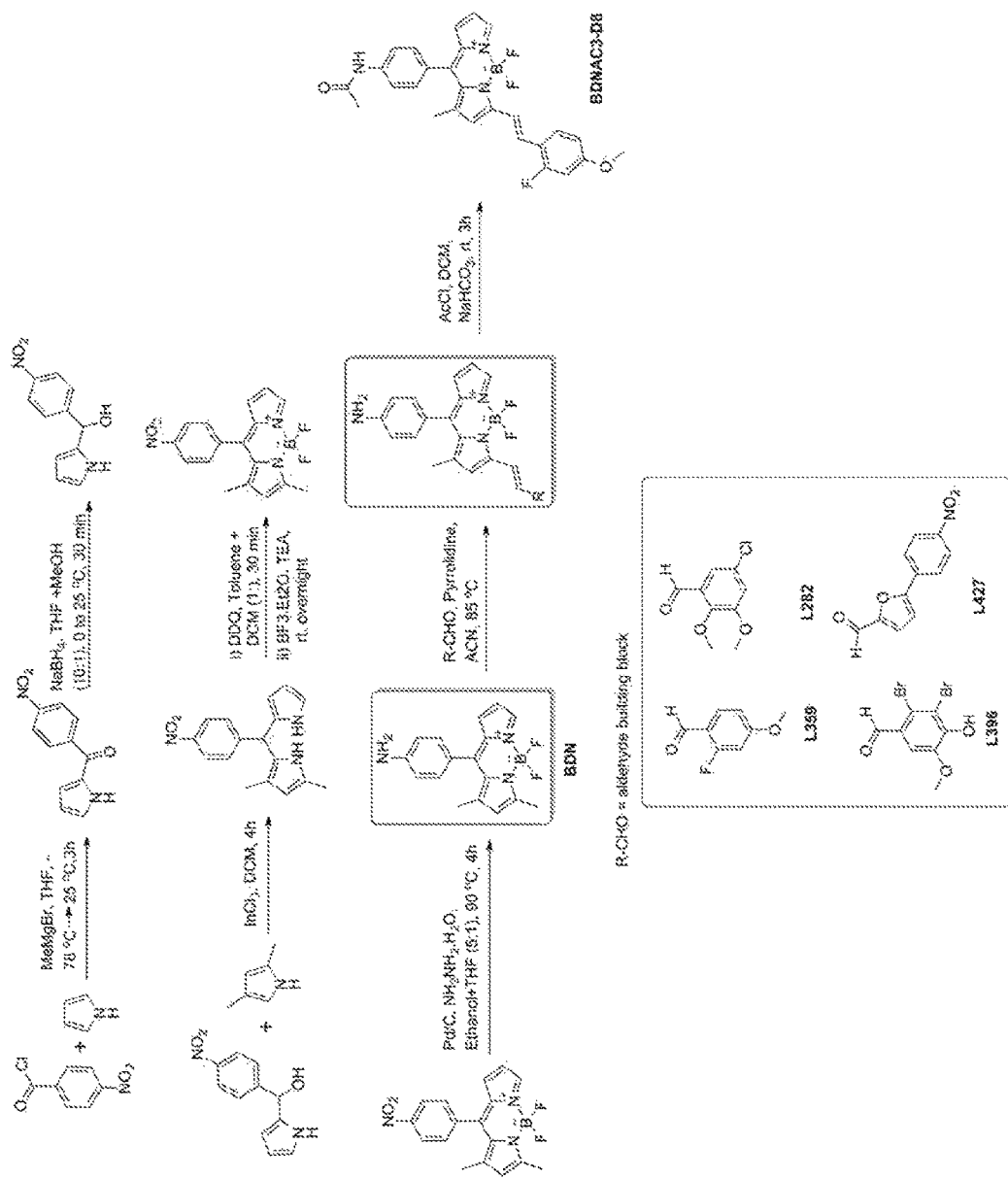
FIG. 1 shows a synthetic scheme for amyloid targeting biofilm sensors (A).
Figure 1:
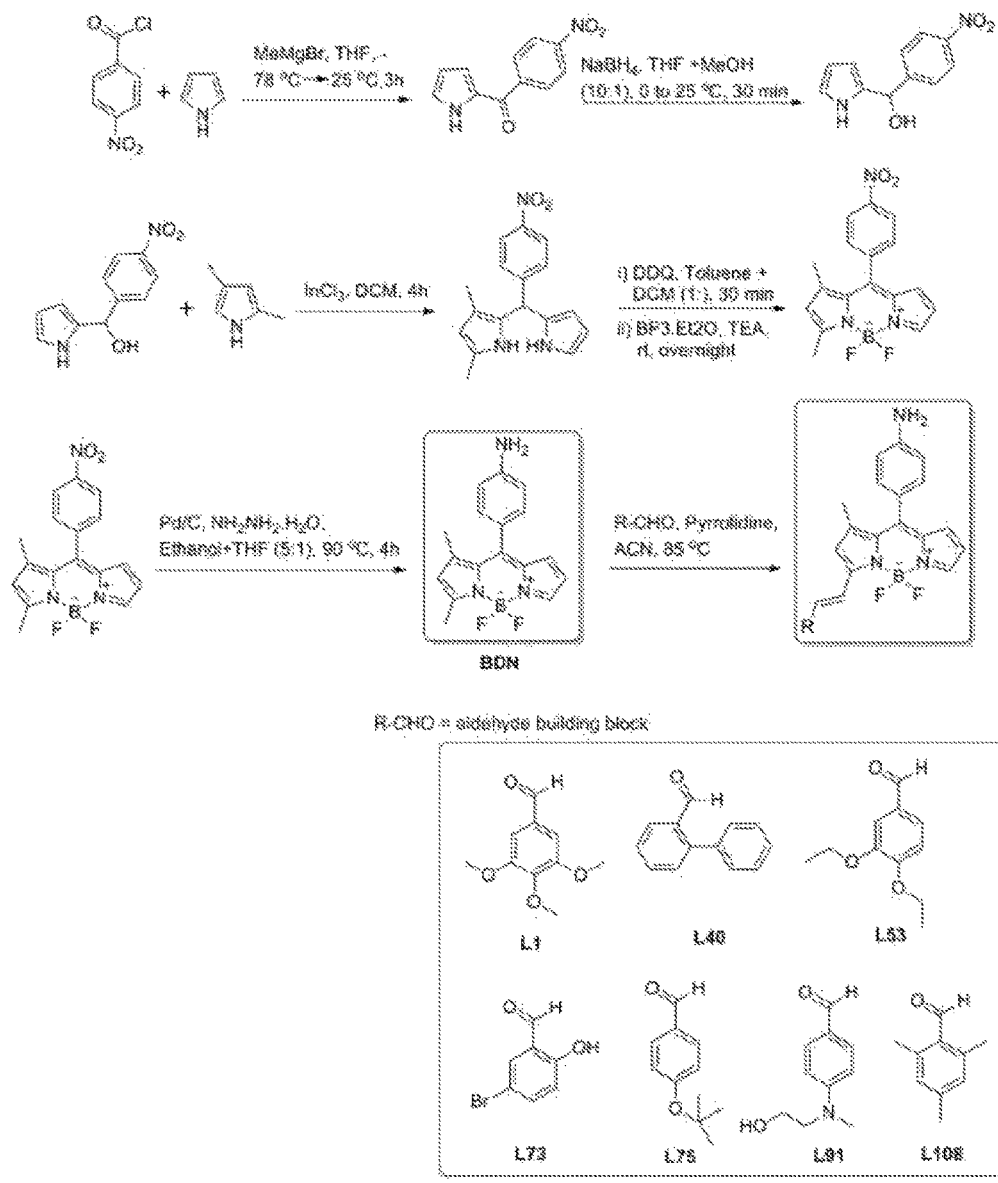

The present inventors surprisingly found that chemicals based on the boron-dipyrromethene (BODIPY) scaffold exhibit the capability to detect biofilms. Further, as said compounds have the capability to produce fluorescence signals they can be used to detect living communities of bacteria forming a biofilm. Therefore, the compounds of the invention are the first biofilm sensors allowing non-destructive in vivo detection. Moreover, the BODIPY-based sensors provide detection sensitivity towards Pseudomonas aeruginosa. Two different types of sensors are found. The first type allows the detection of amyloid protein structures, specifically the detection of the Fap protein of P. aeruginosa, an important component of the biofilm matrix. The second type of sensors specifically binds to bacterial cells that contain high levels of cyclic-di-guanosine-monophosphate (GMP), an internal signal for the biofilm life form.

Thus, in a first aspect, the present invention is thus directed to a compound having the structure of formula (I)

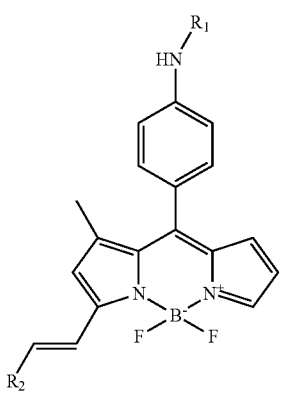

(I)

wherein $R_1$ is H or C(O)—$R_3$,
$R_3$ is $C_{1-10}$ alkyl, and
$R_2$ is substituted or unsubstituted $C_{6-14}$ aryl or a 5-8 membered heteroaryl group comprising 1-4 heteroatoms selected from the group consisting of N, O and S.

"Alkyl", as used herein, refers to a saturated or unsaturated hydrocarbon containing 1-10 carbon atoms including both acyclic and cyclic structures (such as methyl, ethyl, propyl, isopropyl, butyl, isobutyl, sec-butyl, pentyl, hexyl, cyclopropyl, cyclobutyl, cyclopentyl, cyclohexyl, propenyl, butenyl, cyclohexenyl and the like). In preferred embodiments, the alkyl contains 1-6 carbon atoms and in even more preferred embodiments of the invention, the alkyl is a $C_1$-alkyl.

The term "substituted", as used herein, means that any one or more hydrogens on the designated atom or ring is replaced with a selection from the indicated group, provided that the designated atom's normal valency is not exceeded, and that the substitution results in a stable compound. When a substituent is keto (i.e., =O), then 2 hydrogens on the atom are replaced. On the other "unsubstituted" relates to a moiety in which the hydrogen atoms of an alkyl are not substituted for by other atoms or chemical groups.

The term "aryl", as used herein, alone or in combination refers to a substituted or unsubstituted aromatic group, which may be optionally fused to other aromatic or non-aromatic cyclic groups. Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. The aryl groups of the $R_2$ substituent contain 6-14 carbon atoms. In preferred embodiments the aryl group contains 6 carbon atoms.

"Heteroaryl", as used herein, means a monovalent unsaturated aromatic carbocyclic group having a single ring (e.g., pyrridyl or furyl) or multiple condensed rings (e.g., indolizinyl or benzothienyl) and having at least one hetero atom, such as N, O, or S, within the ring, which can optionally be unsubstituted or substituted. Heteroaryl groups include, but are not limited to furanyl, imidazolyl, isothiazolyl, isoxazolyl, 1,2,3-oxadiazoyl, 1,2,5-oxadiazolyl, oxazolyl, pyrazinyl, pyrazolyl, pyridazinyl, pyridinyl, pyrimidinyl, pyrrolyl, tetrazolyl, thiazolyl, thiophenyl, triazinyl and 1,2,3-triazolyl. The heteroaryl group in the compounds of the present invention is a 5-8 membered ring. In preferred embodiments, the ring is 5 membered. The number of heteroatoms is 1-4. In various embodiments, the heteroaryl group contains one heteroatom selected from the group consisting of N, O and S. In various other embodiments of the invention, the heteroatom of the heteroaryl group is O.

In various embodiments of the invention, $R_2$ is

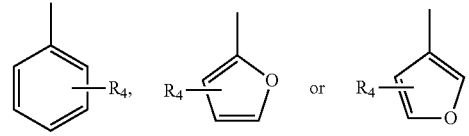

and $R_4$ is selected from the group consisting of H, halogen, alkoxy, hydroxy, nitrobenzene, benzene and tertiary amine.

The term "halogen", as used herein, refers to an atom of chlorine, bromine, fluorine, iodine. The term "alkoxy", as used herein, alone or in combination refers to an alkyl, alkenyl or alkynyl group bound through a single terminal ether linkage. Examples of alkoxy groups include, but are not limited to, methoxy, ethoxy, n-propoxy, iso-propoxy, n-butoxy, 2-butoxy, tert-butoxy, n-pentoxy, 2-pentoxy, 3-pentoxy, isopentoxy, neopentoxy, n-hexoxy, 2-hexoxy, 3-hexoxy, 3-methylpentoxy, fluoromethoxy, difluoromethoxy, trifluoromethoxy, chloromethoxy, dichloromethoxy, and trichloromethoxy. "Hydroxy", as used herein, means an —OH group. The nitrobenzene substituent has the following structure:

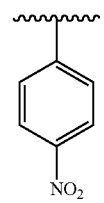

The term "tertiary amine", as used herein, refers to amines in which the nitrogen atom is attached through its three valences to three separate carbon atoms which can be carbon atoms of the same or different hydrocarbon groups that can be alkyl, alkenyl, alkynyl, aryl, alkaryl or aralkyl.

In further various embodiments of the invention, the compound of the invention is selected from the group consisting of

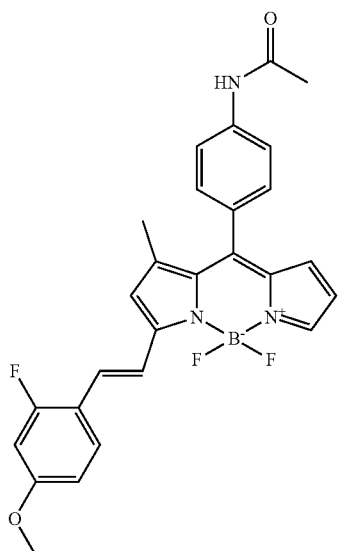
(1)
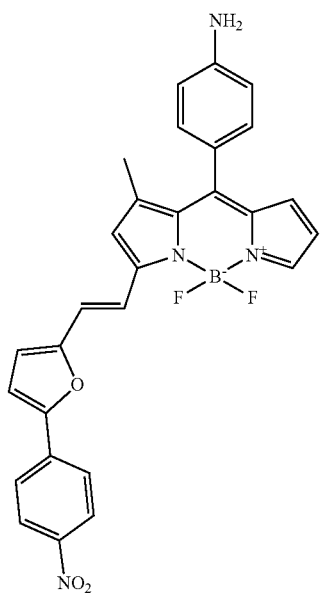
(4)
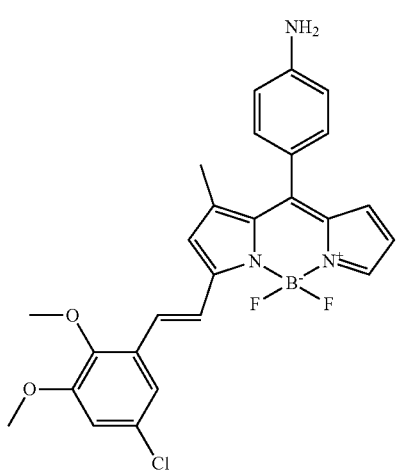
(2)
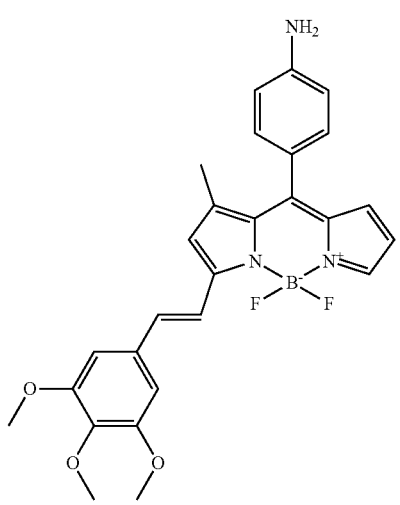
(5)
(3)
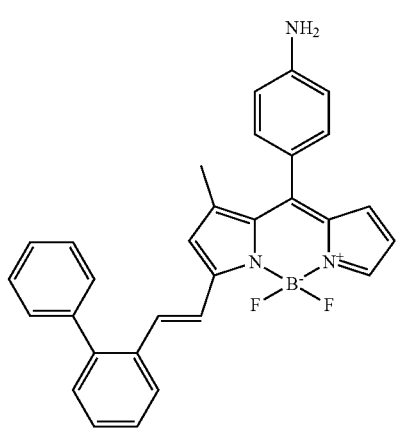
(6)

(7) 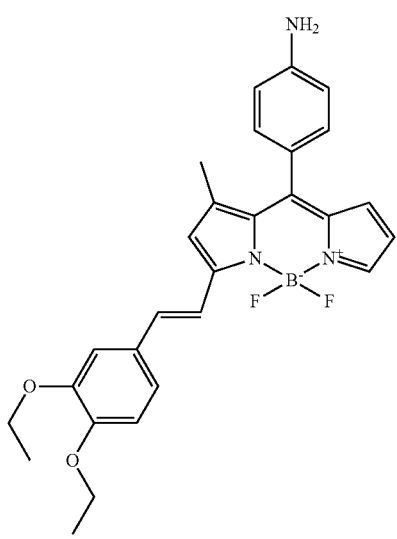
(8) 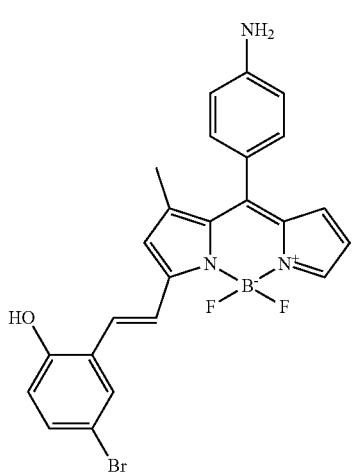
(9) 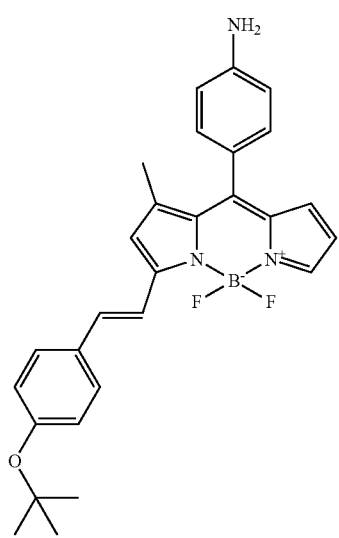
(10) 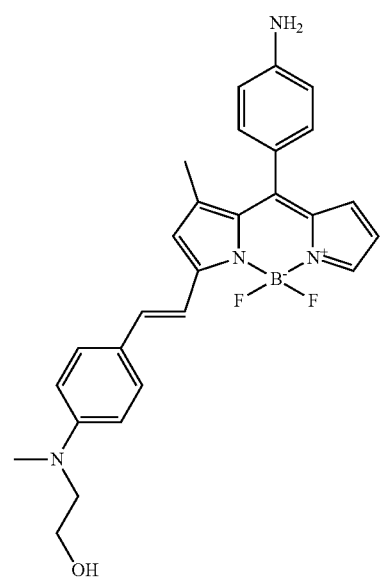
(11) 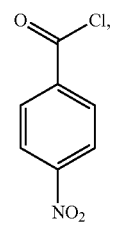
In a second aspect of the invention, the invention relates to a method for the preparation of a compound of the present invention, comprising:
a) reacting the compound of formula (II) with the compound of formula (III) to form the compound of formula (IV)
(II) 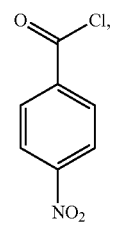
(III) 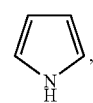

-continued

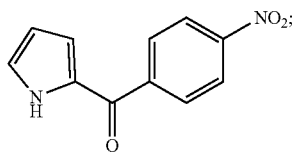
(IV)

b) reducing the compound of formula (IV) to form the compound of formula (V)

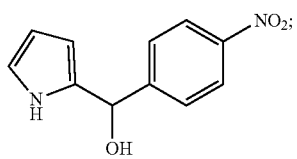
(V)

c) reacting the compound of formula (V) with the compound of formula (VI) to form the compound of formula (VII)

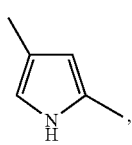
(VI)

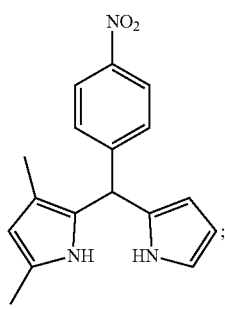
(VII)

d) reacting the compound of formula (VII) with boron trifluoride diethyl etherate to form the compound of formula (VIII)

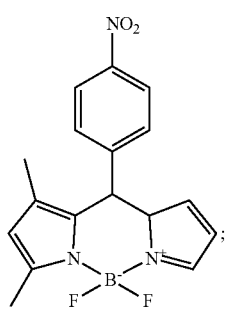
(VIII)

e) reacting the compound of formula (VIII) with $NH_2NH_2$ to form the compound of formula (IX)

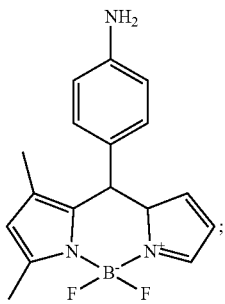
(IX)

f) reacting the compound of formula (IX) with $R_2$—CHO to form the compound of formula (X)

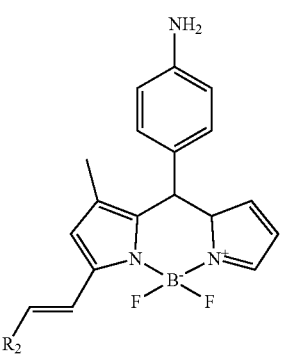
(X)

g) and optionally reacting the compound of formula (X) with $HCO_2R_3$ to form the compound of formula (XI)

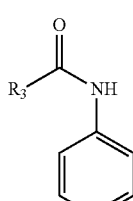
(XI)

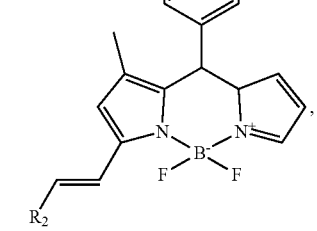

wherein
$R_2$ is substituted or unsubstituted $C_{6-14}$ aryl or a 5-8 membered heteroaryl group comprising 1-4 heteroatoms selected from the group consisting of N, O and S; and
$R_3$ is $C_{1-10}$ alkyl.

The term "reacting" as used with regard to the method of manufacturing the compound of the invention refers to contacting the educts under conditions that allow formation of the product. "Reducing" or "reduction" is any chemical reaction that involves the gaining of electrons. It refers to the side that accepts electrons. In the present case, it refers to the gain of electrons of the compound of formula (IV) to form the compound of formula (V).

In various embodiments of the preparation method of the invention, step (a) is carried out at 25 to 78° C. for 2 to 5 h; step (b) is carried out at 0 to 25° C. for 15 to 60 minutes; step (c) is carried out for 2 to 6 h; step (d) comprises a first reaction reacting the compound of formula (VII), toluene, dichloromethane for 20 to 60 minutes and a second reaction reacting the product of the first reaction with 2,3-dichloro-5,6-dicyano-1,4-benzoquinone and triethanolamine at 20 to 25° C. for 6 to 10 h; step (e) is carried out at 80 to 100° C. for 3 to 5 h; step (f) is carried out at 80 to 90° C.; and/or step (g) is carried out at 20 to 25° C. for 2 to 4 h.

In a third aspect, the present invention relates to the use of a compound of the present invention for the detection of bacterial biofilms.

"At least one", as used herein, relates to one or more, in particular 1, 2, 3, 4, 5, 6, 7, 8, 9, 10 or more.

"Monitor biofilms" or "detecting biofilms", as interchangeably used herein, relate to quantitatively or qualitatively identifying a biofilm-of-interest. The quantitatively detection refers to a detection method which provides a positive or negative result about the presence of a given biofilm. The qualitatively detection provides results describing the amount and type of the investigated biofilm. As an indicator for the amount or density of the biofilm, the colony forming units (CFU) contained in the biofilm can be determined. The term "biofilm type" relates to the composition of the biofilm. In detail, biofilm type relates to the different species and strains of bacteria forming the biofilm. For example, the compounds of the present invention allow to determine if the biofilm contains Pseudomonas aeruginosa.

A (bacterial) biofilm is any group of bacteria, in which cells aggregate in a self-produced matrix of extracellular polymeric substance (EPS). The EPS is a polymeric conglomeration generally composed of extracellular DNA, proteins, and polysaccharides. Biofilms may form on living or non-living surfaces and can be prevalent in natural, industrial and hospital settings. The microbial cells growing as a biofilm are physiologically distinct from planktonic cells of the same organism, which, by contrast, are single-cells that may float or swim in a liquid medium. "Bacteria" or "bacterial cells", as interchangeably used herein, constitute a large domain of prokaryotic microorganisms. Typically a few micrometers in length, bacteria have a number of shapes, ranging from spheres to rods and spirals. They are prokaryotic, unicellular, and either free-living in soil or water or parasites of plants or animals and appearing singly or in chains.

In various embodiments of the invention, the bacterial biofilm comprises Pseudomonas spp., preferably Pseudomonas aeruginosa. Pseudomonas is a genus of Gram-negative, aerobic gammaproteobacteria, belonging to the family Pseudomonadaceae containing 191 validly described species. The members of the genus demonstrate a great deal of metabolic diversity, and consequently are able to colonize a wide range of niches. P. aeruginosa is a common Gram-negative rod-shaped bacterium that can cause disease in plants and animals, including humans. A species of considerable medical importance, P. aeruginosa is a prototypical "multidrug resistant (MDR) pathogen" that is recognized for its ubiquity, its intrinsically advanced antibiotic resistance mechanisms, and its association with serious illnesses— especially nosocomial infections such as ventilator-associated pneumonia and various sepsis syndromes.

In further various embodiments of the invention, an outer cellular amyloid protein structure is detected or, alternatively, the compound specifically binds to bacterial cells that contain high levels of cyclic-di-guanosine-monophosphate (c-di-GMP). "Outer cellular" or "extracellular", as interchangeably used herein, refers to the space outside the outer cellular membrane of a given prokaryote also known as the extracellular medium. This space does neither include the cytoplasm nor the periplasm. In preferred embodiments of the invention, the term "extracellular" relates to the space covered by the extracellular polymeric substances (EPS) of the biofilm (also denoted the extracellular matrix). The term "amyloid" or "amyloid protein structure", as interchangeably used herein, refers to any of certain insoluble fibrous protein aggregates. The terms "specifically bind" and "specific binding", as used herein, generally refers to the ability of a binding molecule, in particular the compound of the present invention, to preferentially bind to a particular target that is present in a given biofilm. In certain embodiments, a specific binding interaction will discriminate between desirable and undesirable target molecules and cells in a biofilm, in some embodiments more than about 10 to 100-fold or more (e.g., more than about 1000- or 10,000-fold). The term "high levels", as used herein, relates to significant increase of cyclic-di-GMP over cyclic-di-GMP levels found in a reference organism. In preferred embodiments, the reference organism is a wildtype strain of P. aeruginosa denoted PAO1. Alternatively, the reference value for the concentration of cyclic-di-GMP can also be the mean value of two or more wildtype reference strains. In more preferred embodiments, the reference value for the concentration of cyclic-di-GMP is the concentration in PAO1. In a preferred embodiment of the invention, the increased levels are at least 1.5-fold, at least 2-fold, at least 3-fold, at least 4-fold or at least 5-fold higher compared to the above described control/normal state.

In structure, cyclic-di-guanosine-monophosphate (GMP) is a cycle containing only two guanine bases linked by ribose and phosphate. Cyclic di-GMP (also called cyclic diguanylate and c-di-GMP) is a second messenger used in signal transduction in a wide variety of bacteria. The biological role of cyclic di-GMP was first uncovered when it was identified as an allosteric activator of a cellulose synthase found in Gluconacetobacter xylinus in order to produce microbial cellulose. Bacteria in the biofilm mode can have up to 10 fold higher cyclic-di-GMP contents compared with their planktonic counterparts.

In various embodiments of the invention, the biofilm is detected in a sample, which is preferably a biological sample, for example a body fluid, cell or tissue sample. Body fluids comprise, but are not limited to tear fluid, blood, blood plasma, blood serum, breast milk, cerebrospinal fluid, cerumen (earwax), endolymph and perilymph, gastric juice, mucus (including nasal drainage and phlegm), sputum, peritoneal fluid, pleural fluid, saliva, sebum (skin oil), semen, sweat, vaginal secretion, nipple aspirate fluid, vomit and urine. The cell or tissue sample may comprise material originated from any part of the body such as connective tissue, muscle tissue, nervous tissue, and epithelial tissue. In preferred embodiments, the bacterial film is detected in an eye sample or a lung sample. The term "obtaining a sample", as used herein, relates to different methods known in the art that comprise, but not limited to, filter based absorption, biopsy, sentinel node biopsy or removal of blood, bone marrow, sputum or bronchial fluids.

In still further various embodiments, the detection limit is at least $8\times10^8$ CFU/ml. In other preferred embodiments, the detection limit is at least $5\times10^9$ CFU/ml, $1\times10^{10}$ or $5\times10^{10}$. A colony forming unit (CFU) is a unit used to estimate the number of viable bacteria in a sample or biofilm. Viable is defined as the ability to grow and multiply under controlled conditions. In various embodiments of the invention, the compound specifically binds to a Fap protein of *P. aeruginosa*. Preferably, the Fap protein is FapB or FapC.

In various embodiments, the biofilm is detected on a silicon surface and/or the biofilm is detected on the surface of a contact lens, catheter or implant device. The catheter is preferably a urinary catheter. The term "implant device" relates to medical implants or tissues that are placed inside or on the surface of the body. Implants can be prosthetics, intended to replace missing body parts. Other implants deliver medication, monitor body functions, or provide support to organs and tissues. Some implants are made from skin, bone or other body tissues. Others are made from metal, plastic, ceramic or other materials. Implants can be placed permanently or they can be removed once they are no longer needed. For example, stents or hip implants are intended to be permanent. But chemotherapy ports or screws to repair broken bones can be removed when they no longer needed.

The term "silicon surface", as used herein, refers to a device having a surface wherein the material of the device and/or the material of the surface comprises or consists of silicon. Silicon materials comprise, but are not limited to sificides, silicon carbide, silane, disilenes, tetrahalides, silicon dioxide, complex silicic acids, ranging from the simplest condensate, disilicic acid ($H_6Si_2O_7$) to linear, ribbon, layer and lattice structures which form the basis of the many silicate minerals and are called polysilicic acids $\{Si_x(OH)_{4-2x}\}_n$, silicon sulfide, silicon that forms a nitride, transition metal complexes containing a metal-silicon bond, polymeric compounds with an (Si—O—Si) backbone, such as PDMS (polydimethylsiloxane) and organosilicon compounds.

In various embodiments of the invention, the bacteria of the biofilm are detected in vivo. Studies that are in vivo are those in which the effects of various biological entities are tested on whole, living organisms, in the present case this relates to biofilms containing living bacteria, as opposed to a partial or dead organism, or those done in vitro, i.e., in a laboratory environment using test tubes, petri dishes etc.

After being applied to the biofilm, the compounds of the present invention may be detected by different microscopy techniques. The compounds can be applied directly on the surface on which the biofilm of interest is formed. Such surface may be a contact lens, a catheter or an implant device. However, the biofilm of interest may also be present in a probe or sample. Such sample may be an eye sample or a lung sample.

The object on which the biofilm of interest is present can be directly treated with the compound of the present invention. It is neither required to fix the cells contained in the biofilm nor to permeabilize said cells. It is therefore considered a non-destructive method. Thus, the compound of the present invention can be applied to living cells in the biofilm. Due to its fluorescence, the compounds of the present invention provide specific signals after being exposed to a light wavelength that activates the emission of the fluorescence signal. This emission may be measured by with a fluorescence microscope. For the detection of the fluorescence of the compound of the present invention, the TRITC channel may be used.

Microscope techniques that allow the detection of the fluorescence signals of the compounds of the present invention include, but are not limited to fluorescence microscopy, confocal microscopy, single plane illumination microscopy and light sheet fluorescence microscopy, deconvolution microscopy, super-resolution microscopy and serial time encoded amplified microscopy (STEAM). However, in case it may advantageous to measure the fluorescence of the compound of the present invention in parallel series, it may be possible to use a plate reader to monitor the signal of the present compound.

EXAMPLES

Materials and Methods
Synthesis and Characterization of a BODIPY-Structure Fluorescent Bio-Film Sensors General Synthetic Procedure for BODIPY (BDN and BDNAC):

Synthesis of BDN intermediate: Synthetic procedure for the synthesis of BDN intermediate was followed from previously publication of Kang et al. (N. Y. Kang, S. C. Lee, S. J. Park, H. H. Ha, S. W. Yun, E. Kostromina, N. Gustaysson, Y. Ali, Y. Chandran, H. S. Chun, M. Bae, J. H. Aim, W. Han, G. K. Radda and Y. T. Chang, Angew. Chem. Int. Edit., 2013, 52, 8557).

General Procedure for She synthesis of BDNAC:
Condensation reaction with aldehyde: To a solution of BODIPY Aniline (BDN) (x eq.) in dry acetonitrile (ACN) was added with corresponding aldehyde (4x eq.), followed by pyrridine (6x eq.) and refluxed at 85° C. for 5 min. The crude condensed BODIPY compound was finally purified by silica gel chromatography in 7:3 hexane and ethyl acetate mixture.

Acylation: The purified compound (0.02 mili moles) from the above step was dissolved in dichiorometnane (DCM) and added with 100 μL of saturated solution of NaHCO3, followed by acetyl chloride (5 eq.) at 0° C. Then the reaction mixture was stirred at room temperature for 30 minutes. The acetylated compound was purified by silica gel chromatography in 7:3 hexane and ethyl acetate mixture.

Synthetic Material and Method:
All reactions were performed in oven-dried glassware under a positive pressure of nitrogen. Unless otherwise noted, starting materials and solvents were purchased from Aldrich and Acros organics and used without further purification. Analytical TLC was carried out on Merck 60 F254 silica gel plate (0.25 mm layer thickness) and visualization was done with UV light. Column chromatography was performed on Merck 60 silica gel (230-400 mesh). NMR spectra were recorded on a Bruker Avance 300 MHz NMR spectrometer. Chemical shifts are reported as 5 in units of parts per million (ppm) and coupling constants are reported as a J value in Hertz (Hz). Mass of all the compounds was determined by LC-MS of Agilent Technologies with an electrospray ionization source. Spectroscopic measurements were performed on a fluorometer and UV/VIS instrument, Synergy 4 of bioteck company and Gemini XS fluorescence plate reader. Relative quantum efficiencies were calculated by comparing the areas under the corrected emission spectrum. The following equation was used to calculate quantum yield.

$$\Phi_x = \Phi_{st}(I_x/I_{st})(A_{st}/A_x)(\eta_x^2/\eta_{st}^2),$$

wherein "$\Phi_{st}$" is the reported quantum yield of the standard, "I" is the integrated emission spectrum, "A" is the absorbance at the excitation wavelength, and "η" is the refractive index of the solvents used. The subscript "x" denotes unknown and "st" denotes standard. Rhodamine B was used as standard.

3D-SIM Super Resolution Images
Precultured *P. aeruginosa* (PAO1-GFP) in ABTGC media was inoculated in 8 well chamber plates with 1:200 dilution rates and incubated for 20 h at 37° C. incubator. Next day, 2 µL of 100 µM of the tested compound was treated in 200 µL cultured bacteria and incubated in 37° C. incubator for 1 h. All of supernatants were removed before observation of images. Images were taken with ×100 magnification oil lens (Zeiss ELYRA PS.1, Jena, Germany). Images under TRITC (Fluorescein isothiocyanate) channel were taken before acquiring images by the compounds under TRITC channel. Two images taken under different channels were processed to super resolution images and finally merged.

Surface Plasmon Resonance (SPR)

Amyloids were prepared in HEPES buffer (0.01 M HEPES, pH 7.4, 0.15 M NaCl, 3 mM EDTA and 0.005% P20). Amyloid fibers were fragmented with sonication at 80 Hz for 10 s and centrifuged at 14 000 g for 30 s to remove any large fibers. Concentrate (40 µL) was mixed with 10 mM sodium acetate (120 µL), pH 5.5 right before immobilization.

SPR experiments were performed at 25° C. using Biacore T-200 biosensor with research grade CM5-S sensor chips (Biacore, GE Healthcare). Carboxymethylated CM5-S chips were activated using 70 µL of 0.2 M 1-ethyl-3-[3-(dimethylamino)propyl] carbodiimide hydrochloride (EDC) and 0.05 M N-hydroxysuccinimide (NHS) in a 1:1 ratio. Amyloid in sodium acetate solution (100 µL) was injected over the activated surface until an immobilization level of 7700 response units (RU) was reached. Ethanolamine hydrochloride (1.0 M), pH 8.5 was injected across the surface for 5 min to block any residual activated-unreacted carboxyl groups. Compounds were dissolved into HEPES buffer containing final concentration of 5% DMSO and serially diluted to 340 nM, 1.03, 3.09, 9.26, 27.78, 83.33 µM. Tht+ was prepared similarly as positive control. Replicates of the diluted compounds were injected across a unmodified flow cell and amyloid-immobilized flow cell in a serial manner for association phase of 60 s followed by dissociation phase of 5 min. Regeneration was not performed since all compounds exhibit complete dissociation within the dissociation duration. The chip surface was rinsed using HEPES buffer. All sensorgrams were double-referenced with responses from unmodified channel and blank HEPES buffer injections. Equilibrium responses from the compounds were plotted against logarithmic of their corresponding concentrations where the binding affinities were calculated from 50% saturation.

Generation of Eye Infection Model

*P. aeruginosa* (PAO1-GFP) was grown at 37° C. in ABTGC media for 16 h. 500 µL of cultured PAO1-GFP was transferred to 1.5 mL Eppendorf tube and centrifuged at 14 000 g for 3 min. Supernatant was removed and pellet was washed with PBS buffer 3 times. Finally, pellet was resuspended in 250 µL of PBS buffer.

Mice were anesthetized ketamine/xylazine by peritoneal injection before scratches were made in cornea with blade. PAO1-GFP (1 µL, 2×107~108 CFU) dissolved in PBS buffer was treated in left eye and PBS buffer was treated in right eye. *P. aeruginosa* inoculated mice were incubated for 2 days before in vivo experiments. Animal handling was in accordance with the Institutional Aminal Care and Use Committee of Singapore Bioimaging Consortium (Agency of Science, Technology and Research, Singapore).

Immunohistochemistry

Rabbit polyclonal antisera targeting *P. aeruginosa* Fap was obtained from BioGenes (Berlin, Germany). Briefly, rabbits were immunized with 100 µg of purified FapC subunit at day 0 and again after 7, 14, 28, and 70 days. The rabbits were sacrificed after 77 days and antisera collected. The antisera showed an ELISA titer of >1:200 000 against purified FapC compared to a titer of 1:300 for the corresponding preimmune sera.

The OCT freezing media embedded sections were cleared by incubating with 1% gelatin PBS buffer for 30 min and remaining solution was removed before incubating with Fap anti-immune serum solution in 1% gelatin PBS buffer for 2 h at 37° C. Samples were washed 3 times with 400 µL washing buffer (1% gelatin, 0.1% triton×100 in PBS) before incubating with secondary antibody linked with Cy5 fluorophore for 1 h at 37° C. Finally, samples were examined with fluorescent microscope after 3 times washing with washing buffer (2.5% tween 20 in PBS).

Preparation of Bacterial Coating Implant

One bacterial colony (PAO1-GFP) was picked up from the plate to inoculate an overnight culture in LB (Luria Broth) media in 37° C. incubator with 110 rpm/min for 20 h. Silicone tubes (Ole Dich) were cut with a thickness of 4 mm and were sterilized in 0.5% NaClO for overnight. Next day, 25 mL of overnight cultured media was transferred to 50 mL conical tube and pellet was collected by centrifuging at 3000 rpm for 10 min. Subsequently, pellet was suspended with 2 mL of LB media before optical density was observed under 600 nm wavelength.

Sterilized silicone was washed twice in 0.9% NaCl solution. Silicone tubes (8 pieces) in 50 mL flask were incubated with 10 mL of diluted bacteria (OD600=0.1) in 0.9% NaCl solution in rotationary shaker at 37° C. with 110 rpm/min for 20 h.

Generation of Implant Model

After anesthesia of mice with ketamine/xylazine mix by intraperitoneal injection, the mouse was placed ventral side up on plate. Fur was clipped and the skin was swabbed with 70% ethanol. An incision of approximately 0.5-1 cm was made in the left groin area. Then an implant prepared the day before was inserted into peritoneal cavity via the incision. The incision was closed with a suture and healed on a warm pad at 26-28° C.

Example 1: Screening for Biofilm Detection Compounds

Figure 2:
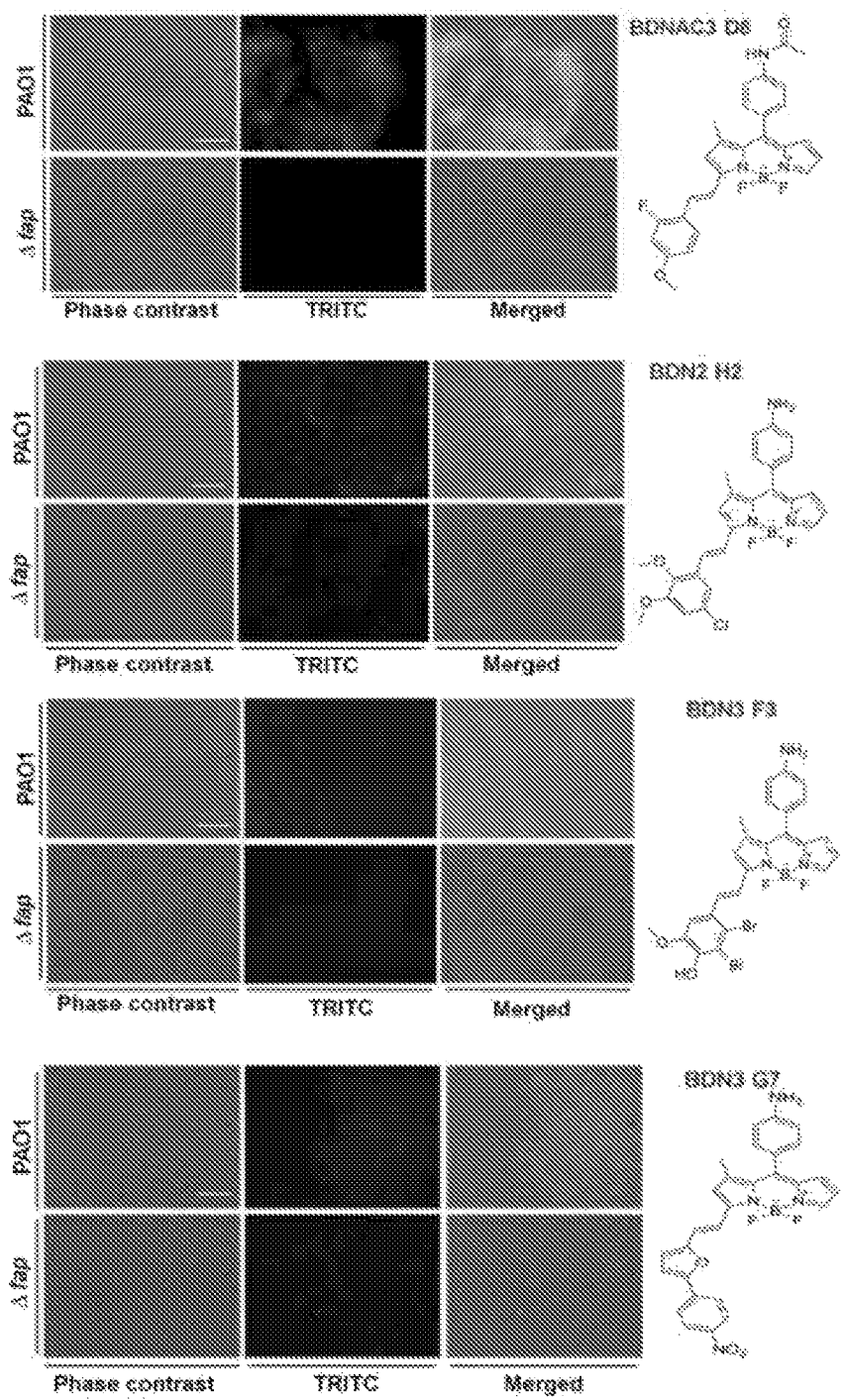
FIG. 2 shows the staining images of four amyloid targeting probes and seven compounds identified that target biofilm cells with high level of cyclic-di-GMP conditions. (A) Fluorescence images of four compounds from screening for targeting amyloid in biofilm and the structures of isolated compounds. All isolated compounds were shown stronger staining intensity in biofilms which were generated with the Pseudomonas strain PAO1 compared to PAO1 Δfap which by genetic modifications is unable to synthesize amyloid components. (B) Fluorescence images with seven compounds, which were isolated from biofilms under high level of cyclic-di-GMP conditions and those compounds structures. Biofilms under high and low levels of cyclic-di-GMP conditions were established by means of two mutant PAO1 strains, wspF and yhjH, respectively. Scale bar=10 µm.
Figure 2:
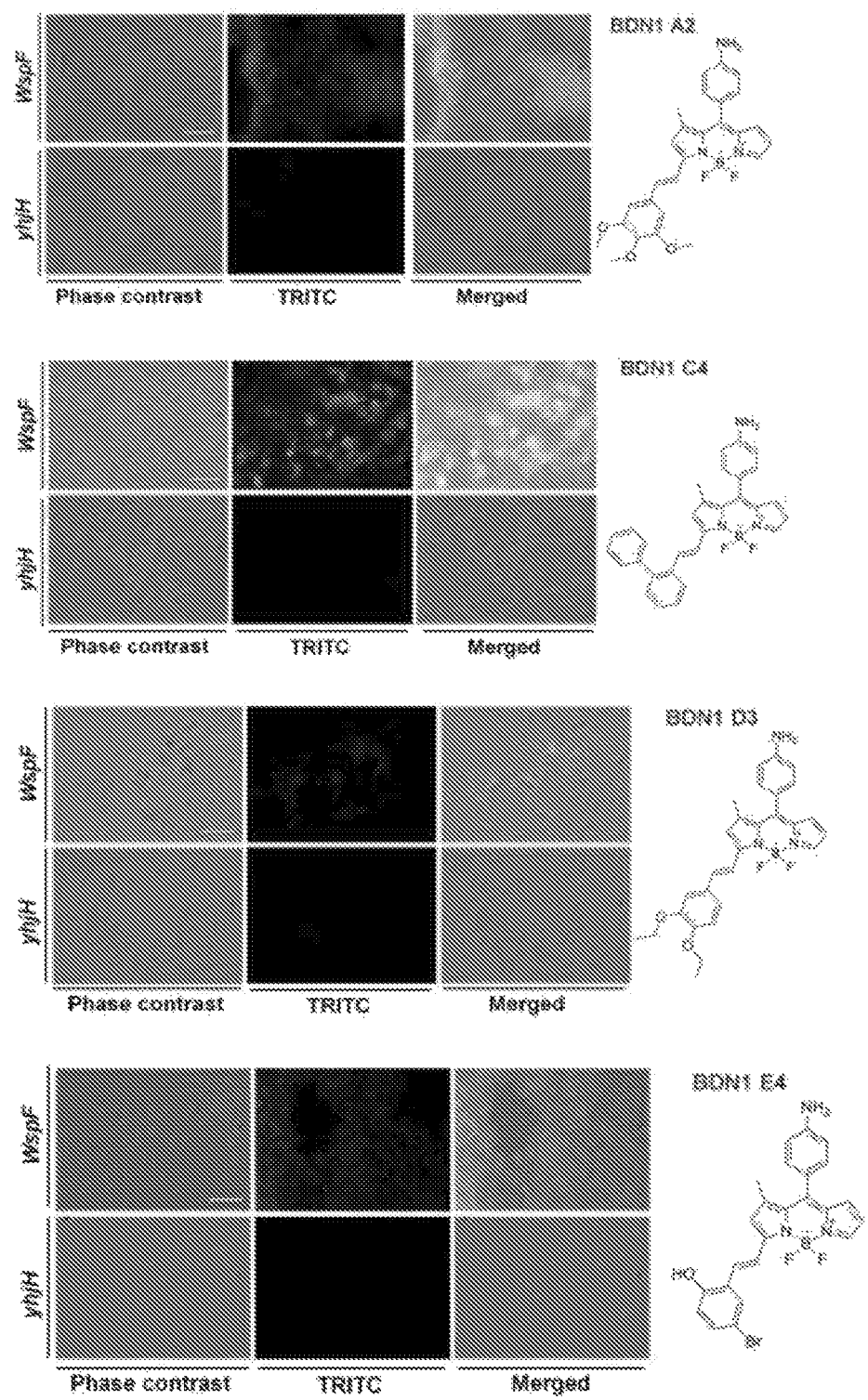

All synthesized compounds were screened in two different established biofilm forming conditions. First, compounds were applied for targeting amyloid structures in biofilms. Amyloid is known as key component for initiating biofilm forming after attaching on surfaces. The wild type, PAO1 strain which normally produces biofilm well is used with a negative control, PAO1 Δfap mutant which doesn't synthesize amyloid component due to deletion of the FAP operon. All compounds were screened against biofilms formed by these two strains for identifying hits that only target the PAO1 biofilm. As results, total four compounds were isolated as amyloid targeting compounds (cf. compounds (1) to (4)). The fluorescence signal of the tested compounds can be observed in the TRITC channel of a fluorescence microscope. The fluorescence signals of the compounds tested on the PAO1 strain and the negative control strain (GFP tagged *P. aeruginosa* PAO1 Δfap mutant) are shown in FIG. 2(A).

In addition, another screening was done for isolating bio-imaging probes under high cyclic-di-GMP levels. Cyclic-di-GMP is known as signaling molecule in *P. aeruginosa*. Biofilm formation is closely connected to the level of cyclic-di-GMP. Under high level of cyclic-di-GMP conditions, virulence and motility of *P. aeruginosa* is decreased and components involved in biofilm formation are synthesized. Two different bacterial mutant strains, ΔwspF and pyhjH, were used for isolating bio-imaging probes. The ΔwspF strain maintains a high level of cyclic-di-GMP due to constitutive expression of a diguanylate cyclase which converts 2 GTP to cyclic-di-GMP and the pyhjH strain maintains a low level of cyclic-di-GMP by constitutive expression of a phospho-diesterase which converts cyclic-di-GMP to 2 GTP. Seven compounds were developed as bio-imaging probes which can stain biofilm under high levels of cyclic-di-GMP condition (cf. compounds (5) to (11)). The fluorescence signal of the tested compounds can be observed in the TRITC channel of a fluorescence microscope. The fluorescence signals of the compounds tested on the ΔwspF strain (positive control) and the negative control strain (pyhjH strain) are shown in FIG. 2(B).

Example 2: Synthesis of Compounds Detecting Amyloid Protein Structures and High Levels of Cyclic-Di-GMP in Bacterial Cells of the Biofilm The synthesis of the four compounds detecting amyloid protein structures is shown in FIG. 1(A). The synthesis of the seven compounds detecting high levels of cyclic-di-GMP in bacterial cells of the biofilm is shown in FIG. 1(B).

Figure 3:
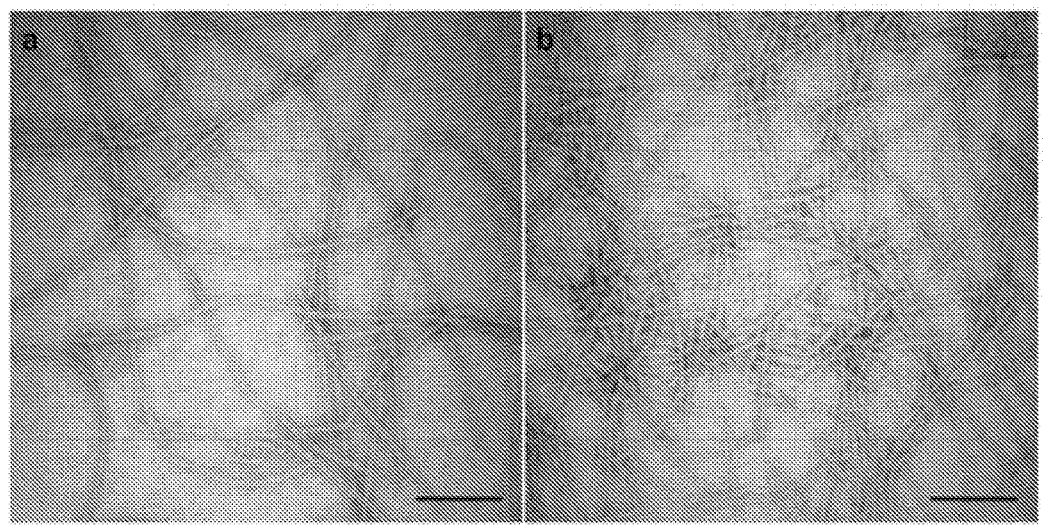
FIG. 3 shows the validation of binding target with a surface plasma resonance assay. In a biofilm screening, two different types of biofilms (biofilm versus amyloid deficient biofilm) were treated with compounds and hits were identified by selective staining of biofilms containing amyloid structures. Thus, the binding affinity of four compounds with the purified amyloid subunit (fibril) protein was validated by surface plasma resonance assay. The subunit protein was immobilized on chips and each of compounds was flowed continuously. Thioflavin T, BDN1 B2 and BDNAC3 E6 were tested with hit compounds. Four amyloid targeting compounds showed higher binding affinity than ThT and two control compounds. (A) TEM images of purified amyloid proteins. Scale bar=400 nm. (B) Surface plasma resonance assay of four amyloid targeting compounds with purified amyloid.
Figure 3:
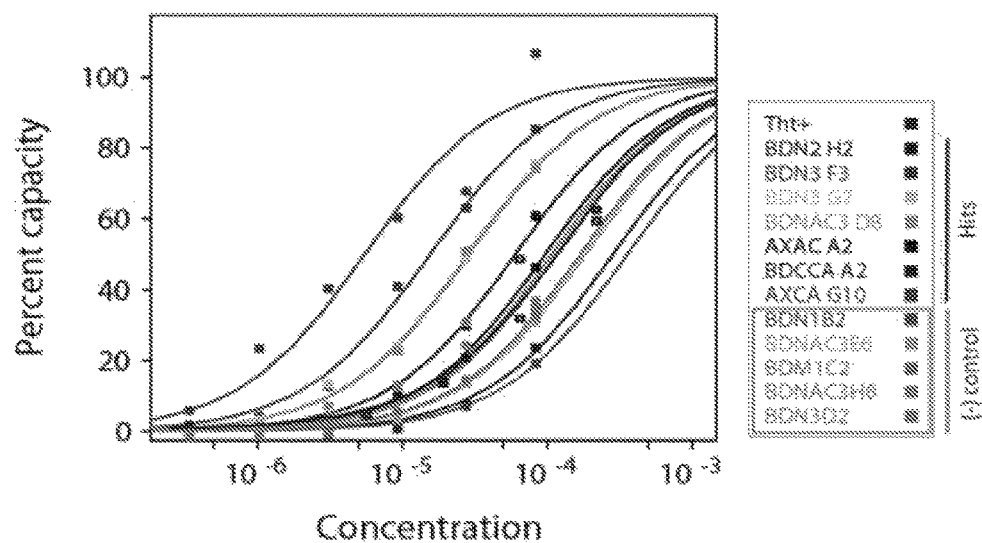

Example 3: Surface Plasma Resonance Assay of Four Amyloid Targeting Compounds with Purified Amyloid First batch of screening was done under varying amyloid expression conditions for specifically isolating amyloid targeting compounds and four compounds were isolated from cell based screening. All of compounds showed stronger staining patterns in intact biofilms synthesized from PAO1 wild type than PAO1 Δfap which does not produce amyloid by deletion of genes (FIG. 2(A)). Finally, four compounds were examined by surface plasma resonance assay whether those have binding specificity with putative target, namely amyloid. Four hit compounds were examined with thioflavin T and two negative controls on chips after immobilizing purified amyloid. As results, all four compounds isolated from cell based screening were shown to have higher binding intensity (KD value; BDNAC3 D8 (29±2 μM), BDN2 H2 (61±3 μM), BDN3 F3 (16±1 μM) and BDN3 G7 (28±5 μM)) than thioflavin T(85±7 μM) then the two negative controls (BDNAC3 E6 (180±30 μM) and BDN1 B2 (360±30 μM)) (FIG. 3(B)).

Example 4: Super Resolution Images after Staining Biofilm Targeting Compounds

Figure 4:
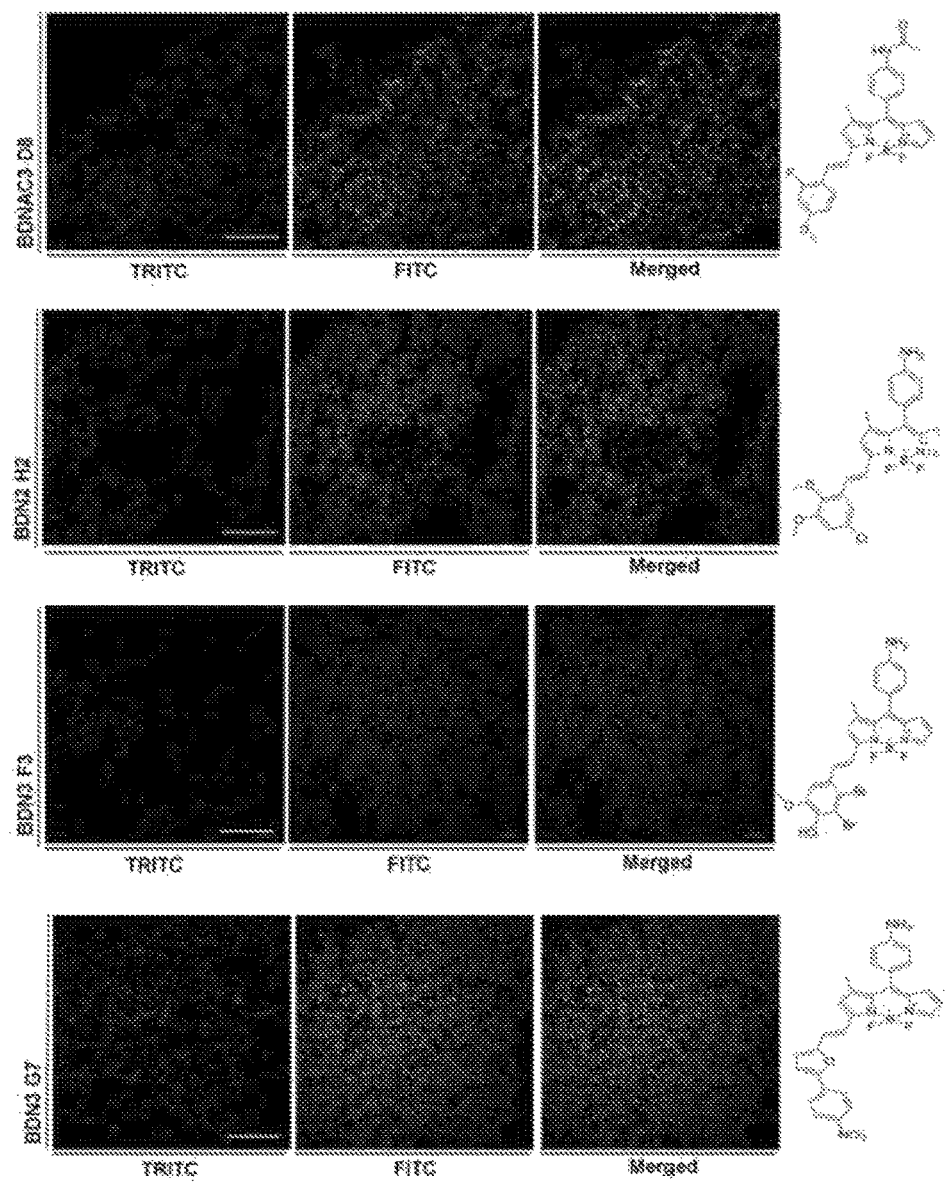
FIG. 4 shows super resolution images after staining with biofilm targeting compounds (four amyloid hits and seven high cyclic-di-GMP hits). Images were taken under confocal laser scanning microscope and processed for super resolution images. 1 day-old biofilm was incubated with four amyloid targeting compounds and seven cyclic-di-GMP targeting compounds for 1 hour and removed before taking images. (A) Super resolution images of four amyloid targeting compounds. (B) Super resolution images of seven compounds from high level of cyclic-di-GMP condition. Scale bar=10 µm.
Figure 4:
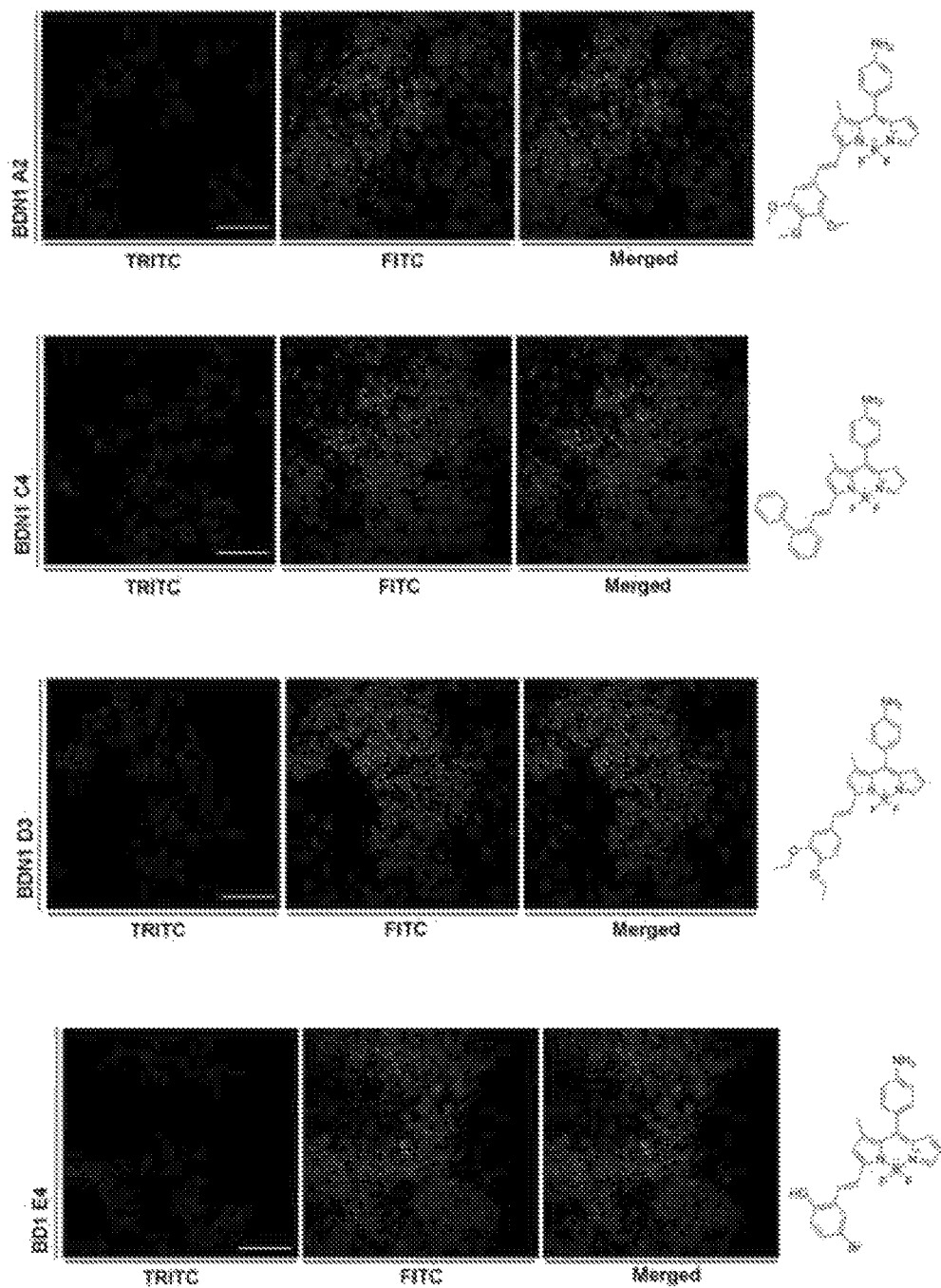

Staining images of all eleven validated hit compounds were taken with confocal microscope and super resolution images were acquired by processing. 1 μM of the four amyloid targeting compounds, respectively, were incubated with 1-day old biofilm from PAO1-GFP culture. Images were taken under TRITC channels for observation of individual cells in biofilm subsequently another image was taken under TRITC channels for observing compounds signals in biofilms. Finally, those images were processed to super resolution images. The signals observed for the tested compounds stained particles and thread like structures in P. aeruginosa population. Amyloid structures are visualized by four amyloid targeting compounds among whole biofilm. Stained structures are amyloid structures which are one of the components among biofilms (FIG. 4(A)).

Binding targets of seven compounds which were isolated from high level of cyclic-di-GMP conditions are investigated because expression profiles of bacteria are extremely changed by changing the cyclic-di-GMP levels. Thus, the seven validated compounds were tested, respectively, with 1-day old biofilm under confocal microscope for acquiring clues from high resolution images. Compounds signals detected under TRITC channel were distributed in the biofilm rather than staining of individual cells. Synthesized and secreted molecules which are one of the components of the biofilm may be targeted by the seven compounds that are specific for high level of cyclic-di-GMP conditions (FIG. 4(B)).

Figure 5:
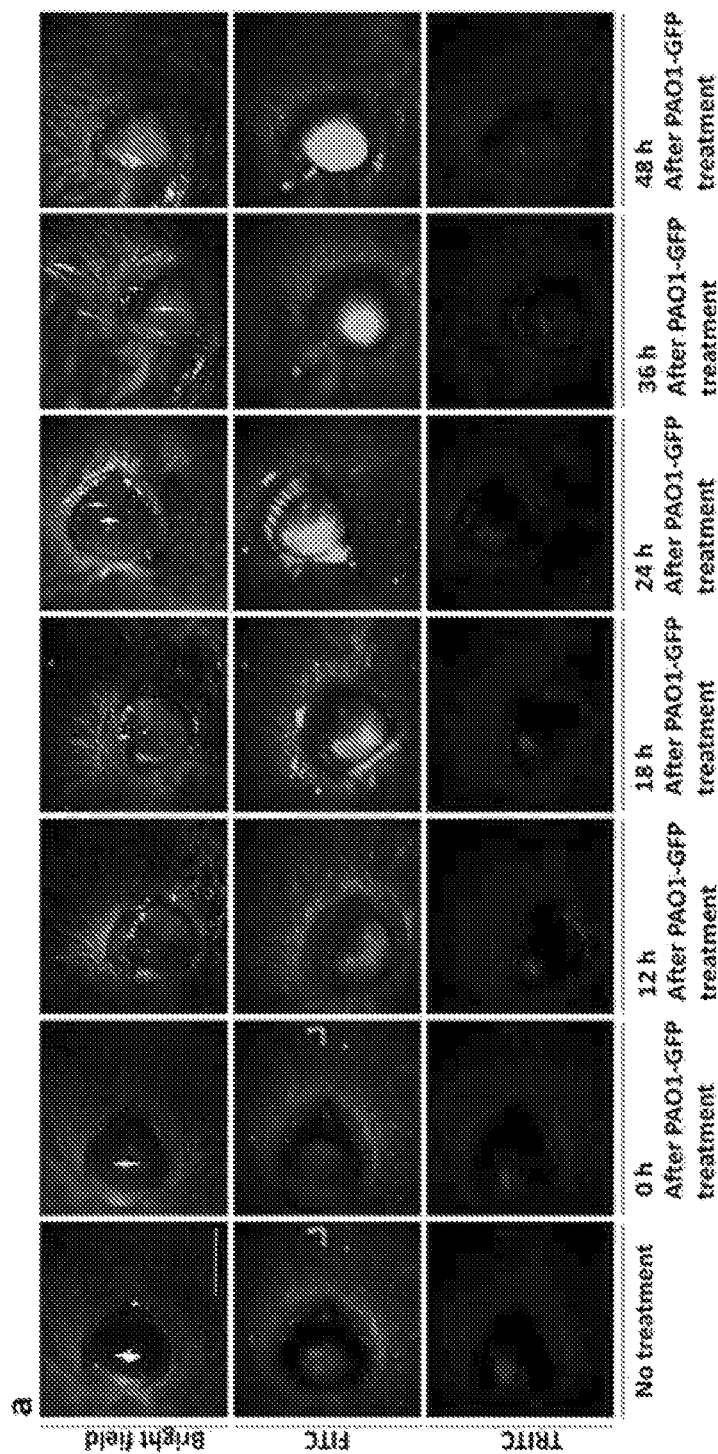
FIG. 5 shows in vivo application of two amyloid targeting compounds, BDNAC3 D8 and BDN2 H2 in established eye infection model. (A) Propagation of Pseudomonas aeruginosa (PAO1-GFP) after infecting into mouse eyes. GFP signals were detected after 12 hours later after infecting bacteria and signals were fully saturated after 24 hours later; Scale bar=2 mm. (B) Tests of amyloid targeting compounds in eye infection models. The model was generated by inoculation of a GFP tagged P. aeruginosa PAO1 strain into the eye after making scratches in cornea. Images were taken in bright field and TRITC from ketamine/xylazine anesthetized mice and compounds signals were examined under TRITC channel after incubation with compounds for 10 minutes at room temperature. Scale bar=2 mm.
Figure 5:
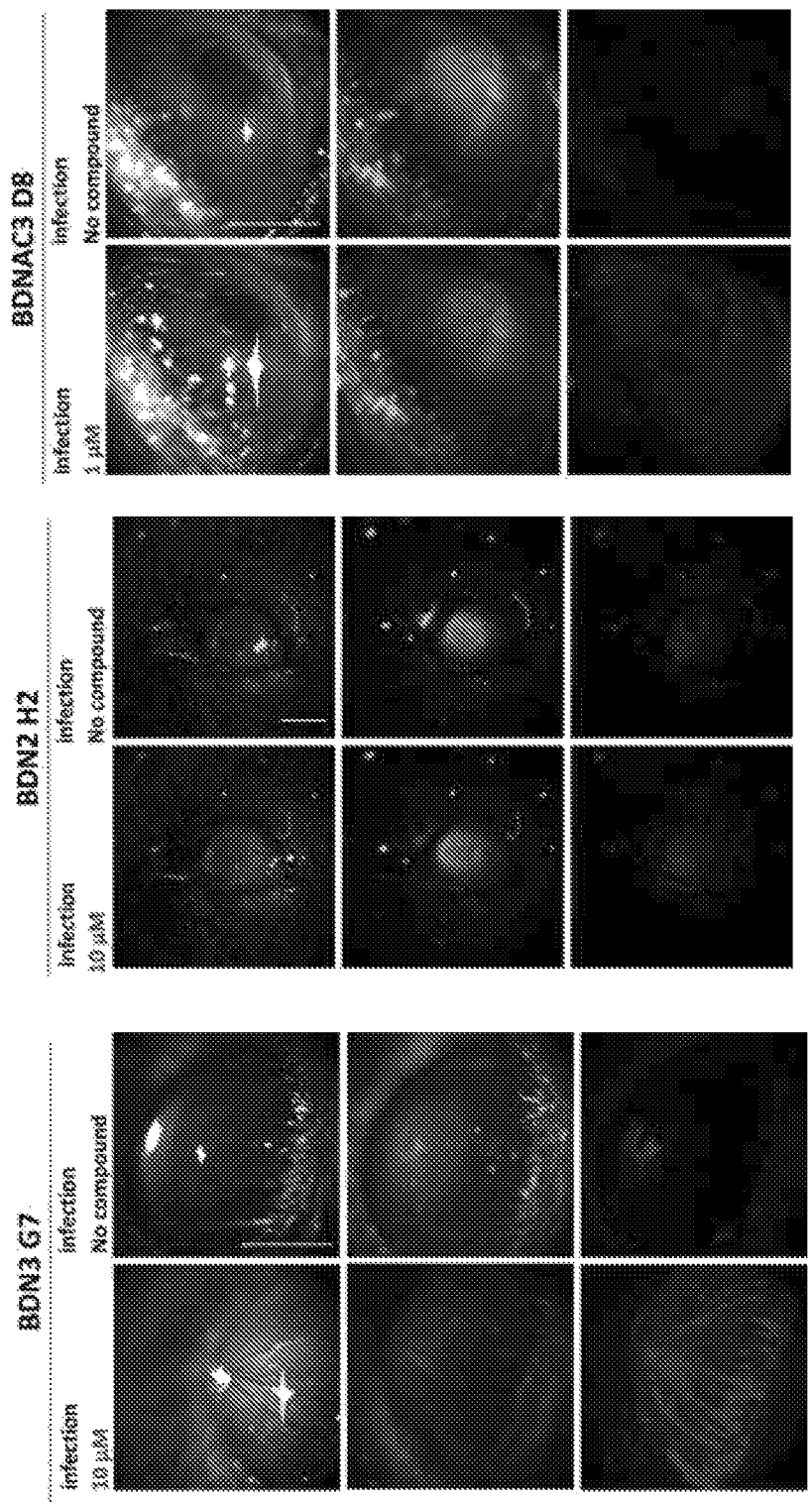

Example 5: In Vivo Application of Two Amyloid Targeting Compounds, BDNAC3 D8 and BDN2 H2, in an Established Eye Infection Model Biofilm is stained by amyloid targeting compounds through interacting with FAP proteins which is one of the components for intact biofilm. Thus, amyloid targeting compounds were tested in eye infection model which is one of the naturally reported symptoms of P. aeruginosa containing biofilms. Eye infection model was generated in black mouse. In cornea, there is no immune system even low dose of inoculation of bacteria will make biofilm well without side effects. Cornea in black mouse was scratched using blade after anesthesia with ketamine/xylazine and was treated cultured P. aeruginosa (PAO1-GFP) for 2 days (FIG. 5(A)). Eyes were examined under stereomicroscope as time dependent manner. As control test, images were taken from eyes after 10 minutes incubation with mock treatment at room temperature. GFP signals were detected after 12 hours incubation with P. aeruginosa-GFP bacteria.

Fluorescence signals under TRITC channel were checked to confirm infection on cornea and amyloid compounds were tested under TRITC channel after incubation for 10 minutes. Infected eyes were visualized with BDN2 H2, BDNAC3 D8 and BDN3 G7 (FIG. 5(B)). Isolated compounds from established cell based screening format show possibility to detect biofilm in vivo.

Example 6: Test of CDy11 (BDNAC3 D8) in an Implant Model

The inventors also applied a mouse implant model to test the capacity of CDy11 (BDNAC3 D8) to detect P. aeruginosa biofilms in a surgical format. Silicone tubes were precolonized by bacteria and subsequently inserted into the peritoneal cavity 1 day before the experiment. BALB/c mice were assigned to each of the two groups and 100 μM CDy11 (200 μL) was injected into the mice via the peritoneal cavity 2 h before recovering the implants. As a mock control, a similar volume of buffer was injected into the second set of mice. In addition, CDy11 was injected into a set of mice which had been installed with uncolonized silicone tubes in the peritoneal cavity.

Figure 6:
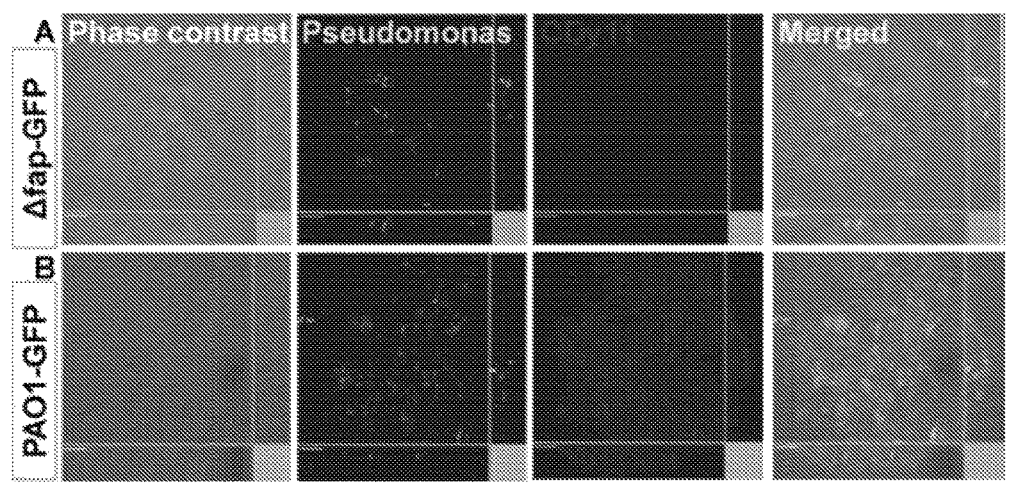
FIG. 6 shows a test of CDy11 (BDNAC3 D8) in implant model. CLSM images of a GFP tagged P. aeruginosa PAO1 strain colonizing silicone implants after removal from BALB/c mice at day 1 post insertion. Green fluorescent areas represent P. aeruginosa. Insertion of silicone tube into mice which was precoated with (A) PAO1Δfap-GFP and (B) PAO1-GFP biofilms. Images of the microcolonies adhering to the silicone implants with CDy11. Only PAO1-GFP biofilms coated silicone tube was stained by CDy11; Scale bars=10 µm.

All silicone tubes were collected after 2 h incubation to observe CDy11 fluorescence of the inner surface of the silicone tube by means of laser confocal scanning microscopy. As a result, biofilm coated silicone tube using PAO1Δfap-GFP strain which does not produce Fap in the EPS was not stained by CDy11 (FIG. 6(A)). P. aeruginosa biofilm (PAO1-GFP) coated silicone tubes were specifically stained with CDy11 (FIG. 6(B)) while, biofilms under same condition without CDy11 showed only the GFP signal (data not shown). The silicone tubes without P. aeruginosa precoating were also examined by injection of same amount of CDy11. Immune cells had moved into the silicone tubes but those were not stained by CDy11 (data not shown).

The invention has been described broadly and generically herein. Each of the narrower species and subgeneric groupings falling within the generic disclosure also form part of the invention. This includes the generic description of the invention with a proviso or negative limitation removing any subject-matter from the genus, regardless of whether or not the excised material is specifically recited herein. Other embodiments are within the following claims. In addition, where features or aspects of the invention are described in terms of Markush groups, those skilled in the art will recognize that the invention is also thereby described in terms of any individual member or subgroup of members of the Markush group.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," containing", etc. shall be read expansively and without limitation. The word "comprise" or variations such as "comprises" or "comprising" will accordingly be understood to imply the inclusion of a stated integer or groups of integers but not the exclusion of any other integer or group of integers. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The content of all documents and patent documents cited herein is incorporated by reference in their entirety.

The invention claimed is:

1. A method for detecting bacterial biofilms, the method comprising:

providing a compound having a structure of Formula (I)

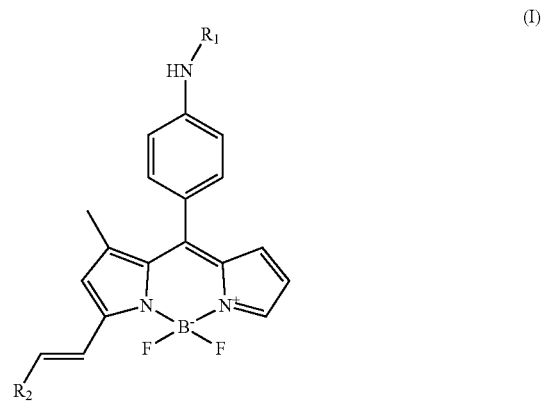

wherein $R_1$ is H or C(O)—$R_3$,
$R_3$ is a $C_{1-10}$ alkyl, and
$R_2$ is a substituted or unsubstituted $C_{6-14}$ aryl or a 5-8 membered heteroaryl group comprising 1-4 heteroatoms selected from the group consisting of N, O and S, and contacting the compound with a sample suspected of comprising the bacterial biofilm.

2. The method according to claim 1, wherein the bacterial biofilm comprises *Pseudomonas aeruginosa*.

3. The method according to claim 1, wherein an outer cellular amyloid protein structure is detected.

4. The method according to claim 1, wherein the compound specifically binds to bacterial cells that contain high levels of cyclic-di-guanosine-monophosphate (GMP).

5. The method according to claim 1, wherein the bacterial film is detected in an tissue sample from the eye or lung.

6. The method according to claim 1, wherein the detection limit is $8 \times 10^8$ CFU/ml.

7. The method according to claim 1, wherein the compound specifically binds to a Fap protein of *Pseudomonas aeruginosa*.

8. The method according to claim 1, wherein the biofilm is detected on a silicon surface.

9. The method according to claim 1, wherein the biofilm is detected on the surface of a contact lens, catheter or implant device.

* * * * *